(12) United States Patent
Hayward et al.

(10) Patent No.: US 7,160,991 B1
(45) Date of Patent: Jan. 9, 2007

(54) VASCULAR ENDOTHELIAL GROWTH FACTOR POLYPEPTIDES

(75) Inventors: Nicholas Kim Hayward, Paddington (AU); Gunther Weber, Stockholm (SE); Sean Grimmond, Taringa (AU); Magnus Nordenskjold, Stockholm (SE); Catharina Larsson, Stockholm (SE)

(73) Assignees: Ludwig Institute for Cancer Research, Stadelhoferstrasse (CH); Licentia Ltd., Helsinki (FI)

( * ) Notice: Subject to any disclaimer, the term of this patent is extended or adjusted under 35 U.S.C. 154(b) by 328 days.

(21) Appl. No.: 09/238,088

(22) Filed: Jan. 27, 1999

Related U.S. Application Data

(62) Division of application No. 08/765,588, filed on Apr. 25, 1997.

(30) Foreign Application Priority Data

| Mar. 2, 1995 | (AU) | PN1457 |
| Nov. 20, 1995 | (AU) | PN6647 |
| Dec. 22, 1995 | (AU) | PN7274 |

(51) Int. Cl.
*A61K 38/18* (2006.01)
*C07K 14/475* (2006.01)
*C07K 14/49* (2006.01)

(52) U.S. Cl. .......................... 530/399; 530/350; 514/12
(58) Field of Classification Search ................. 530/300, 530/350, 399; 514/2, 12
See application file for complete search history.

(56) References Cited

U.S. PATENT DOCUMENTS

| 5,073,492 A | 12/1991 | Chen et al. |
| 5,194,596 A * | 3/1993 | Tischer et al. |
| 5,219,739 A | 6/1993 | Tischer et al. |
| 5,338,671 A | 8/1994 | Scalice et al. |
| 5,607,918 A * | 3/1997 | Eriksson et al. |
| 5,840,693 A | 11/1998 | Eriksson et al. |
| 5,928,939 A | 7/1999 | Eriksson et al. |

FOREIGN PATENT DOCUMENTS

| WO | WO 90/13649 | 11/1990 |
| WO | WO 95/24473 | 9/1995 |

OTHER PUBLICATIONS

Lewin . Science 237(1570) 1987.*
Reeck et al. Cell 50(667) 1987.*
Breier, et al. (1992) "Expression of Vascular Endothelial Growth Factor During Embryonic Angiogenesis and Endothelial Cell Differentiation", *Development* 114:521–532.

Ferrara, et al. (1991) "Purification and Cloning of Vascular Endothelial Growth Factor Secreted by Pituitary Folliculostellate Cells", *Methods in Enzymology* 198:391–405.

Houck, et al. (1991) "The Vascular Endothelial Growth Factor Family: Identification of a Fourth Molecular Species and Characterization of Alternative Splicing of RNA", *Molecular Endocrinology* 5(12) :1806–1814.

Keck, et al. (1989) "Vascular Permeability Factor, an Endothelial Cell Mitogen Related to PDGF", *Science* 2461309–1312.

Lagercrantz, et al. (1996) "Expression of the VEGF–Related Factor Gene in Pre– and Postnatal Mouse", *Biochemical and Biophysical Research Communications* 220:147–152.

Leung, et al. (1989) "Vascular Endothelial Growth Factor is a Secreted Angiogenic Mitogen", *Science* 246:1306–1309.

Lyttle, et al. (Jan. 1994) "Homologs of Vascular Endothelial Growth Factor are Encoded by the Poxvirus Orf Virus", *Journal of Virology* 68(1) :84–92.

Sharma, et al. (1995) "Nucleotide Sequence and Expression of the Porcine Vascular Endothelial Growth Factor", *Biochimica et Biophysica Acta* 1260:235–238.

Tischer, et al. (Dec. 29, 1989) "Vascular Endothelial Growth Factor:A New Member of the Platelet–Derived Growth Factor Gene Family", *Biochemical and Biophysical Research Communications* 165(3) :1198–1206.

Tischer, et al. (Jun. 25, 1991) "The Human Gene for Vascular Endothelial Growth Factor", *The Journal of Biological Chemistry* 266(18) :11947–11954.

Weindel, et al. (Mar. 31, 1992) "Aids–Associated Kaposi's Sarcoma Cells in Culture Express Vascular Endothelial Growth Factor", *Biochemical and Biophysical Research Communications* 183(3) :1167–1174.

* cited by examiner

*Primary Examiner*—Christine J. Saoud
(74) *Attorney, Agent, or Firm*—Scully, Scott, Murphy & Presser

(57) ABSTRACT

The present invention relates generally to an isolated molecule having vascular endothelial growth factor-like properties and to a genetic sequence encoding same. The molecule will be useful in the development of a range of therapeutics and diagnostics useful in the treatment, prophylaxis and/or diagnosis of conditions requiring enhanced or diminished vasculature and/or vascular permeability. The molecule of the present invention is also a useful effector of primary and central neurons and is capable of inducing astroglial proliferation.

8 Claims, 40 Drawing Sheets

FIG. 1A

```
1    TCGGCCTCC GAAACC ATG AAC TTT CTG
                       Met Asn Phe Leu
                        1

50   CTT GCC TTG CTG CTC TAC CTC CAC
     Leu Ala Leu Leu Leu Tyr Leu His
                  15

98   CCC ATG GCA GAA GGA GGA GGG CAG
     Pro Met Ala Glu Gly Gly Gly Gln
              30                   35

146  ATG GAT GTC TAT CAG CGC AGC TAC
     Met Asp Val Tyr Gln Arg Ser Tyr
          45                  50

194  GAC ATC TTC CAG GAG TAC CCT GAT
     Asp Ile Phe Gln Glu Tyr Pro Asp
     60                  65

242  TCC TGT GTG CCC CTG ATG CGA TGC
     Ser Cys Val Pro Leu Met Arg Cys
                      80

290  CTC GAG TGT GTG CCC ACT GAG GAG
     Leu Glu Cys Val Pro Thr Glu Glu
                      95

338  CGG ATC AAA CCT CAC CAA GGC CAG
     Arg Ily Lys Pro His Gln Gly Gln
              110                 115
```

FIG. 1B

| | |
|---|---|
| CTG TCT TGG GTG CAT TGG AGC<br>Leu Ser Trp Val His Trp Ser<br>  5                    10 | 49 |
| CAT GCC AAG TGG TCC CAG GCT GCA<br>His Ala Lys Trp Ser Gln Ala Ala<br> 20                   25 | 97 |
| AAT CAT CAC GAA GTG GTG AAG TTC<br>Asn His His Glu Val Val Lys Phe<br>                40 | 145 |
| TGC CAT CCA ATC GAG ACC CTG GTG<br>Cys His Pro Ile Glu Thr Leu Val<br>             55 | 193 |
| GAG ATC GAG TAC ATC TTC AAG CCA<br>Glu Ile Glu Tyr Ile Phe Lys Pro<br>        70                   75 | 241 |
| GGG GGC TGC TGC AAT GAC GAG GGC<br>Gly Gly Cys Cys Asn Asp Glu Gly<br>        85                   90 | 289 |
| TCC AAC ATC ACC ATG CAG ATT ATG<br>Ser Asn Ile Thr Met Gln Ile Met<br>100                  105 | 337 |
| CAC ATA GGA GAG ATG AGC TTC CTA<br>His Ile Gly Glu Met Ser Phe Leu<br>                120 | 385 |

FIG. 1C

```
386    CAG CAC AAC AAA TGT GAA TGC AGA
       Gln His Asn Lys Cys Glu Cys Arg
           125             130

434    GAA AAT CCC TGT GGG CCT TGC TCA
       Glu Asn Pro Cys Gly Pro Cys Ser
       140             145

482    CAA GAT CCG CAG ACG TGT AAA TGT
       Gln Asp Pro Gln Thr Cys Lys Cys
                       160

530    TGC AAG GCG AGG CAG CTT GAG TTA
       Cys Lys Ala Arg Gln Leu Glu Leu
                   175

578    AAG CCG AGG CGG TGAGCCGGGC AGGAG
       Lys Pro Arg Arg
                   190

630    GAACCAGATC TCTCACCAGG
```

FIG. 1D

```
CCA AAG AAA GAT AGA GCA AGA CAA            433
Pro Lys Lys Asp Arg Ala Arg Gln
            135

GAG CGG AGA AAG CAT TTG TTT GTA            481
Glu Arg Arg Lys His Leu Phe Val
        150                     155

TCC TGC AAA AAC ACA GAC TCG CGT            529
Ser Cys Lys Asn Thr Asp Ser Arg
    165                 170

AAC GAA CGT ACT TGC AGA TGT GAC            577
Asn Glu Arg Thr Cys Arg Cys Asp
180                 185

GAAGG AGCCTCCCTC AGCGTTTCGG                629

```
1     CC ATG AGC CCT CTG CTC CGC CGC
         Met Ser Pro Leu Leu Arg Arg
          1               5

48    CTG GCC CCC GCC CAG GCC CCT GTC
      Leu Ala Pro Ala Gln Ala Pro Val
                       20

96    CAG AGG AAA GTG GTG TCA TGG ATA
      Gln Arg Lys Val Val Ser Trp Ile
                   35

144   CAG CCC CGG GAG GTG GTG GTG CCC
      Gln Pro Arg Glu Val Val Val Pro
                   50                55

192   GTG GCC AAA CAG CTG GTG CCC AGC
      Val Ala Lys Gln Leu Val Pro Ser
               65               70

240   GGC TGC TGC CCT GAC GAT GGC CTG
      Gly Cys Cys Pro Asp Asp Gly Leu
           80              85

288   CAA GTC CGG ATG CAG ATC CTC ATG
      Gln Val Arg Met Gln Ile Leu Met
                              100

336   GGG GAG ATG TCC CTG GAA GAA CAC
      Gly Glu Met Ser Leu Glu Glu His
                    115
```

FIG. 2B

| | |
|---|---|
| CTG CTG CTC GCC GCA CTC CTG CAG<br>Leu Leu Leu Ala Ala Leu Leu Gln<br>           10                    15 | 47 |
| TCC CAG CCT GAT GCC CCT GGC CAC<br>Ser Gln Pro Asp Ala Pro Gly His<br>    25                    30 | 95 |
| GAT GTG TAT ACT CGC GCT ACC TGC<br>Asp Val Tyr Thr Arg Ala Thr Cys<br> 40                    45 | 143 |
| TTG ACT GTG GAG CTC ATG GGC ACC<br>Leu Thr Val Glu Leu Met Gly Thr<br>                  60 | 191 |
| TGC GTG ACT GTG CAG CGC TGT GGT<br>Cys Val Thr Val Gln Arg Cys Gly<br>           75 | 239 |
| GAG TGT GTG CCC ACT GGG CAG CAC<br>Glu Cys Val Pro Thr Gly Gln His<br>           90                  95 | 287 |
| ATC CGG TAC CCG AGC AGT CAG CTG<br>Ile Arg Tyr Pro Ser Ser Gln Leu<br>    105                   110 | 335 |
| AGC CAG TGT GAA TGC AGA CCT AAA<br>Ser Gln Cys Glu Cys Arg Pro Lys<br>120                    125 | 383 |

FIG. 2C

| | | | | | | | | |
|---|---|---|---|---|---|---|---|---|
| 384 | AAA | AAG | GAC | AGT | GCT | GTG | AAG | CCA |
| | Lys | Lys | Asp | Ser | Ala | Val | Lys | Pro |
| | | | | 130 | | | | 135 |
| 432 | CGT | CCC | CAG | CCC | CGT | TCT | GTT | CCG |
| | Arg | Pro | Gln | Pro | Arg | Ser | Val | Pro |
| | | | 145 | | | | 150 | |
| 480 | CCC | TCC | CCA | GCT | GAC | ATC | ACC | CAT |
| | Pro | Ser | Pro | Ala | Asp | Ile | Thr | His |
| | 160 | | | | | 165 | | |
| 528 | GCC | CAC | GCT | GCA | CCC | AGC | ACC | ACC |
| | Ala | His | Ala | Ala | Pro | Ser | Thr | Thr |
| | | | | | 180 | | | |
| 576 | GCT | GCC | GCT | GCC | GAC | GCC | GCA | GCT |
| | Ala | Ala | Ala | Ala | Asp | Ala | Ala | Ala |
| | | | | 195 | | | | |

FIG. 2D

| | |
|---|---|
| GAC AGG GCT GCC ACT CCC CAC CAC<br>Asp Arg Ala Ala Thr Pro His His<br>140 | 431 |
| GGC TGG GAC TCT GCC CCC GGA GCA<br>Gly Trp Asp Ser Ala Pro Gly Ala<br>155 | 479 |
| CCC ACT CCA GCC CCA GGC CCC TCT<br>Pro Thr Pro Ala Pro Gly Pro Ser<br>170 175 | 527 |
| AGC GCC CTG ACC CCC GGA CCT GCC<br>Ser Ala Leu Thr Pro Gly Pro Ala<br>185 190 | 575 |
| TCC TCC GTT GCC AAG GGC GGG GCT T<br>Ser Ser Val Ala Lys Gly Gly Ala<br>200 205 | 624 |

FIG. 2E

```
 625    AGAGCTCAAC CCAGACACCT GCAGGTGCCG
 685    GACTCAGCAG GGTGACTTGC CTCAGAGGCT
 745    GGTAAAAAAC AGCCAAGCCC CCAAGACCTC
 805    GCCTCTCAGA GGGCTCTTCT GCCATCCCTT
 865    GAGTTGGAAG AGGAGACTGG GAGGCAGCAA
 825    GGAGTACTGT CTCAGTTTCT AACCACTCTG
 985    CTCCCCTCAC TAAGAAGACC CAAACCTCTG
1045    CTGTGACCCC CAACCCTGAT AAAAGAGATG
```

FIG. 2F

| | | | |
|---|---|---|---|
| GAAGCTGCGA | AGGTGACACA | TGGCTTTTCA | 684 |
| ATATCCCAGT | GGGGGAACAA | AGGGGAGCCT | 744 |
| AGCCCAGGCA | GAAGCTGCTC | TAGGACCTGG | 804 |
| GTCTCCTGA | GGCCATCATC | AAACAGGACA | 864 |
| GAGGGGTCAC | ATACCAGCTC | AGGGGAGAAT | 924 |
| TGCAAGTAAG | CATCTTACAA | CTGGCTCTTC | 984 |
| CATAATGGGA | TTTGGGCTTT | GGTACAAGAA | 1044 |
| GAAGGAAAAA | AAAAAAAAA | | 1094 |

FIG. 3A

>VEGF_HUMAN VEGF_HUMAN VASCULAR ENDOTHELIAL
(VASCULAR 215 AA.
LENGTH = 215

SCORE = 181 (92.4 BITS), EXPECT = 6.4e-20,
IDENTITIES = 33/75 (44%), POSITIVES = 48/75

```
QUERY:   31 HQRKVVSWIDVYTRATCQPREVVVPLTVEL
             +++ VV +DVY R+ C+P E +V +  E
SBJCT:   36 NHHEVVKFMDVYQRSYCHPIETLVDIFQEY

QUERY:   91 PTGQHQVRMQILMIR 105
             PT +  + MQI+ I+
SBJCT:   96 PTEESNITMQIMRIK 110
```

SCORE = 76 (38.8 BITS), EXPECT = 0.0011,
IDENTITIES = 12/19 (63%), POSITIVES = 16/19

```
QUERY:  110 QLGEMSLEEHSQCECRPKK 128
             ++GEMS +H+ CECRPKK
SBJCT:  116 HIGEMSFLQHNKCECRPKK 134
```

SCORE = 72 (36.8 BITS), EXPECT = 0.0046,
IDENTITIES = 14/21 (66%), POSITIVES = 15/21

```
QUERY:  202 RCQGRGLELNPDTCRCRKLRR 222
             RC +R LELN  TCRC K RR
SBJCT:  195 RCKARQLELNERTCRCDKPRR 215
```

SCORE = 46 (23.5 BITS), EXPECT = 47.,
IDENTITIES = 6/10 (60%), POSITIVES = 9/10

```
QUERY:  187 DPRTCRCRCR 196
             DP+TC+C C+
SBJCT:  181 DPQTCKCSCK 190
```

FIG. 3B

GROWTH FACTOR PRECURSOR (VEGF)

P = 6.4e-20
(64%)

MGTVAKQLVPSCVTVQRCGGCCPDDGLECV 90
  +       PSCV + RCGGCC D+GLECV
PDEIEYIFKPSCVPLMRCGGCCNDEGLECV 95

POISSON P(2) = 9.1e-12
(84%)

POISSON P(3) = 3.6e-18
(71%)

POISSON P(4) = 7.3e-10
(90%)

FIG. 4A

```
Gap Weight:3.00        Average Match:1.000
Length Weight:0.100    Average Mismatch:-0.900
       Quality:100.9          Length:739
         Ratio:0.175            Gaps:30
Percent                Percent
Similarity:69.703      Identity:69.703
```

```
 28    ATGAGCCCTCTGCTCCGCCGCCTGC
       ||||  | ||||||     |  ||
 17    ATGAACTTTCTGCT.....GTCT..

68    TGCAGCTGGCCCCCGCCCAGGCCCC
       ||| |||    || |   ||| |||
 57    TGCTGCTCTACCTCCACCATGCCAA

118    CACCAGAGGA...............
       |||||
106    AGAAGGAGGAGGGCAGAATCATCAC

140    GTGTATACTCGC.GCTACCTGCCAG
       || |||   ||| |||| ||||||
152    GTCTATCAGCGCAGCTA.CTGCCAT

194    T....GA.....CTGTGGAGCTCAT
       |    ||     |||  ||| ||
201    TCCAGGAGTACCCTGATGAGATCGA

235    CCCAGCTGCGTGACTGTGCAGCGCT
       ||  ||| ||| |  ||  ||| |
239    CCATCCTGTGTGCCCCTGATGCGAT

285    CCTGGAGTGTGTGCCCACTGGGCAG
       ||||||||||||||||||||| | |
289    CCTGGAGTGTGTGCCCACTGAGGAG
```

FIG. 4B

```
TGCTCGCCGCACT.........CC        67
  | | ||| |          |
...TGGGTGCATTGGAGCCTTGCCT       56

TGTCTCCAGCCTGATGCCCCTGGC        117
  ||||||  |||    |||  ||||
GTGGTCCAGGCTGCA.CCCATGGC        105

.AAGTGGTG....TCATGGATAGAT       147
 ||||||||    |||||   |||
GAAGTGGTGAAGTTCATG....GAT       151

CCCCGGGAG...GTGGTGGTGCCCT       193
 ||   |||   ||||||    ||
CCAATCGAGACCCTGGTGGACATCT       200

GGGCACCGTGGCCAAACAGCTGGTG       234
 |  || | |   |||           |
GTACATCTT...CAA.........G       238

GTGGTGGCTGCTGCCCTGACGATGG       284
 | || ||||||||| ||||||  ||
GCGGGGGCTGCTGCAATGACGAGGG       288

CACCAAGTCCGGATGCAGAT.....       329
 | |  ||    ||||||||
TCCAACATCACCATGCAGATTATGC       338
```

FIG. 4C

```
330     ........CCTCATGATCCGGTACC
                ||||| 		       |
339     GGATCAAACCTCA...........C

369     GTCCCTGGAAGAACACAGCCAGTGT
        | | |   | | |||| | | |||
376     GAGCTTCCTACAGCACAACAAATGT

419     GTGCTGTGAAGCCAGACAGGGCTGC
        |       ||| ||||| |
423     G........AGCAAGACAAG.....

469     CGTTCTGTTCCGGGCTGGGACTCTG
        | ||  || |||  ||
443     ...TGTGGCCTTGCTCAGA.....

519     CATCACCCATCCCACTCCAGCCCCA

468     .........................

569     GC..........ACCACCAGCGCCC
        ||          ||| |
469     GCATTTGTTTGTACAA.........

609     TGCCGACGCCGCAGCTTCCTCCGTT
        || | |   |||  ||   ||||
509     TG.CAAAAACACAGACTC...GCGTT

657     AACCCAGACACCTGCAGGTGCCGGA
          |||  |
554     AACGAACGTACTTGCAGATGTGACA
```

FIG. 4D

```
CGAGCAGTCAGC....TGGGGGAGAT     368
 | ||   | ||||    |  || ||||||
CAAG..GCCAGCACATAGGAGAGAT      375

GAATGCAGACCTAAAAAAAAGGACA      418
||||||||||||   |||  ||  || |
GAATGCAGACC...AAAGAAAGATA      422

CACTCCCCACCACCGTCCCCAGCCC      468
           |    ||||
..........AAAATCCC......       442

CCCCCGGAGCACCCTCCCCAGCTGA      518
      ||||| |
...GCGGAGAA..............      467

GGCCCCTCTGCCCACGCTGCACCCA      568
                        |
........................A     468

TGACCCCCGGACCTGCCGCTGCCGC      608
 || || | ||| ||    ||   |
.GATCCGCAGACGTGTAAATGTTCC      508

GCCAAGGGCGGGGC..TTAGAGCTC      656
||   ||||  |||   | |||  |
GC..AAGGCGAGGCAGCTTGAGTTA      553

AGCTGCGAAGGTGA                 695

AGCCGAGGCGGTGA                 592
```

FIG. 5A

```
165SOMSQ.MSF.msf  MSF:687
Type: D Tuesday, June 20, 1995
Check:3140
```

```
                 1
     VEGF165   ATGAACTTTCTGCTGTCTTGGGTG
      SOM175   ATGAGCCCTCTGCTCCGCCGCCTG
   SOM175-e6   ATGAGCCCTCTGCTCCGCCGCCTG
  SOM175-e6&7  ATGAGCCCTCTGCTCCGCCGCCTG
   SOM175-e4   ATGAGCCCTCTGCTCCGCCGCCTG

81
     VEGF165   CACCCATGGCAGAAGGAGGAGGGC
      SOM175   TGCCCCTGGCCACCAGAGGAAAGT
   SOM175-e6   TGCCCCTGGCCACCAGAGGAAAGT
  SOM175-e6&7  TGCCCCTGGCCACCAGAGGAAAGT
   SOM175-e4   TGCCCCTGGCCACCAGAGGAAAGT

161
     VEGF165   CCAATCGAGACCCTGGTGGACATC
      SOM175   GTGGTGGTGCCCTTGACTG.TGGA
   SOM175-e6   GTGGTGGTGCCCTTGACTG.TGGA
  SOM175-e6&7  GTGGTGGTGCCCTTGACTG.TGGA
   SOM175-e4   GTGGTGGTGCCCTTGACTG.TGGA

241
     VEGF165   GATGCGATGCGGGGGCTGCTGCAA
      SOM175   GCAGCGCTGTGGTGGCTGCTGCCC
   SOM175-e6   GCAGCGCTGTGGTGGCTGCTGCCC
  SOM175-e6&7  GCAGCGCTGTGGTGGCTGCTGCCC
   SOM175-e4   GCAGCGCTGTGGTGGCTGCTGCCC
```

FIG. 5B

```
CATTGGAGCCTTGCCTTGCTGCTCTACC
CTGCTCGCCGCACTCCTGCAGCTGGCCC
CTGCTCGCCGCACTCCTGCAGCTGGCCC
CTGCTCGCCGCACTCCTGCAGCTGGCCC
CTGCTCGCCGCACTCCTGCAGCTGGCCC

AGAATCATCACGAAGTGGTGAAGTTCAT
GGTGTCATGGATAGATGTGTATACTCGC
GGTGTCATGGATAGATGTGTATACTCGC
GGTGTCATGGATAGATGTGTATACTCGC
GGTGTCATGGATAGATGTGTATACTCGC

TTCCAGGAGTACCCTGATGAGATCGAGT
GCTCATGGGCACCGTGGCCAAAC..AGC
GCTCATGGGCACCGTGGCCAAAC..AGC
GCTCATGGGCACCGTGGCCAAAC..AGC
GCTCATGGGCACCGTGGCCAAAC..AGC

TGACGAGGGCCTGGAGTGTGTGCCCACT
TGACGATGGCCTGGAGTGTGTGCCCACT
TGACGATGGCCTGGAGTGTGTGCCCACT
TGACGATGGCCTGGAGTGTGTGCCCACT
TGACGATGGCCTGGAGTGTGTGCCCACT
```

FIG. 5C

```
                                    80
TCCACCATGCCAAGTGGTCCCAGGCTG.
CCGCCCAGGCCCCTGTCTCCCAGCCTGA
CCGCCCAGGCCCCTGTCTCCCAGCCTGA
CCGCCCAGGCCCCTGTCTCCCAGCCTGA
CCGCCCAGGCCCCTGTCTCCCAGCCTGA

160
GGATGTCTATCAGCGCAGCTACTGCCAT
G.....CTACCTGC.CAGCC.CCGGGAG
G.....CTACCTGC.CAGCC.CCGGGAG
G.....CTACCTGC.CAGCC.CCGGGAG
G.....CTACCTGC.CAGCC.CCGGGAG

240
ACATCTTCAAGCCATCCTGTGTGCCCCT
TGGTGCCCAG......CTGCGTGACTGT
TGGTGCCCAG......CTGCGTGACTGT
TGGTGCCCAG......CTGCGTGACTGT
TGGTGCCCAG......CTGCGTGACTGT

320
GAGGAGTCCAACATCACCATGCAGATTA
GGGCAGCACCAAGTCCGGATGCAGATCC
GGGCAGCACCAAGTCCGGATGCAGATCC
GGGCAGCACCAAGTCCGGATGCAGATCC
GGGCAGCACCAAGTCCGGATGCAGA...
```

FIG. 5D

```
              321
    VEGF165   TGCGGATCAAACCTCACCAAGGCC
     SOM175   TCATGATCCGG...TACCCGAGCA
  SOM175-e6   TCATGATCCGG...TACCCGAGCA
 SOM175-e6&7  TCATGATCCGG...TACCCGAGCA
  SOM175-e4   ........................

401
    VEGF165   AAGAAAGATAG........AGCAA
     SOM175   AAAAAGGACAGTGCTGTGAAGCCA
  SOM175-e6   AAAAAGGACAGTGCTGTGAAGCCA
 SOM175-e6&7  AAAAAGGACAGTGCTGTGAAGCCA
  SOM175-e4   AAAAAGGACAGTGCTGTGAAGCCA

481
    VEGF165   ..........AAGCA.........
     SOM175   CTCTGCCCCCGGAGCACCCTCCCC
  SOM175-e6   ........................
 SOM175-e6&7  ........................
  SOM175-e4   CTCTGCCCCCGGAGCACCCTCCCC

561
    VEGF165   A..............GATCCGCA
     SOM175   GCACCACCAGCGCCCTGACCCCCG
  SOM175-E6   GCACCACCAGCGCCCTGACCCCCG
 SOM175-e6&7  ........................
  SOM175-e4   GCACCACCAGCGCCCTGACCCCCG

641
    VEGF165   TTGAGTTAAACGAACGTACTTGCA
     SOM175   TAGAGCTCAACCCAGACACCTGCA
  SOM175-e6   TAGAGCTCAACCCAGACACCTGCA
 SOM175-e6&7  ........................
  SOM175-e4   TAGAGCTCAACCCAGACACCTGCA
```

FIG. 5E

```
AGCACATAGGAGAGATGAGCTTCCTACA
GTCAGCTGGGGGAGATGTCCCTGGAAGA
GTCAGCTGGGGGAGATGTCCCTGGAAGA
GTCAGCTGGGGGAGATGTCCCTGGAAGA
............................

GACAAGAA....AATCCCTGTGG......
GACAGGGCTGCCACTCCCCACCACCGTC
GATAG.......................
GATAG.......................
GACAGGGCTGCCACTCCCCACCACCGTC

............................
AGCTGACATCACCCATCCCACTCCAGCC
..........................CC
............................
AGCTGACATCACCCATCCCACTCCAGCC

GACGTGTAAATGTTCCTGCAAAAAC.AC
GACCTGCCGCTGCCGCTGCCGACGCCGC
GACCTGCCGCTGCCGCTGCCGACGCCGC
............................
GACCTGCCGCTGCCGCTGCCGACGCCGC
                         687
GATGTGACAAGCCGAGGCGGTGA
GGTGCCGGAAGCTGCGAAGGTGA
GGTGCCGGAAGCTGCGAAGGTGA
.GTGCCGGAAGCTGCGAAGGTGA
GGTGCCGGAAGCTGCGAAGGTGA
```

FIG. 5F

```
                                         400
GCACAACAAATGTGAATGCAGACC...A
ACACAGCCAGTGTGAATGCAGACCTAAA
ACACAGCCAGTGTGAATGCAGACCTAAA
ACACAGCCAGTGTGAATGCAGACCTAAA
....................CCTAAA

480
.........GCCTTGCTCAGAGCGGAGA
CCCAGCCCCGTTCTGTTCCGGGCTGGGA
............................
CCCAGCCCCGTTCTGTTCCGGGCTGGGA

560
........TTTGTT.....TGTAC..A
CCAGGCCCCTCTGCCCACGCTGCACCCA
CCAGGCCCCTCTGCCCACGCTGCACCCA
............................
CCAGGCCCCTCTGCCCACGCTGCACCCA

640
AGACTCG..CGTTGCAAGGCGAGGCAGC
AGCTTCCTCCGTTGCCAAGGGCGGGGCT
AGCTTCCTCCGTTGCCAAGGGCGGGGCT
............................
AGCTTCCTCCGTTGCCAAGGGCGGGGCT
```

FIG. 6A

```
VEGF165      MNFLLSWVHWSLALLLYLHHAKWSQAAP
SOM175Short  MSPLLRRLL..LAALLQLAPAQ....AP VEGF165      IFQEYPDEIEYIFKPSCVPLMRCGGCCN
SOM175Short  LTVELMGTVAKQLVPSCYTVQRCGGCCP VEGF165      FLQHNKCECRPKK.....DRA.......
SOM175Short  LEEHSQCECRPKKKDSAVKPDRAATPHH VEGF165      CKCSCKNTDSRCKARQLELNERTCRCDK
SOM175Short  HAAPSTTSALTPGPAAAADAAASSVAK

OR....

VEGF165      MNFLLSWVHWSLALLLYLHHAKWSQAAP
SOM175Long   MSPLLRRLL..LAALLQLAPAQ....AP VEGF165      IFQEYPDEIEYIFKPSCVPLMRCGGCCN
SOM175Long   LTVELMGTVAKQLVPSCYTVQRCGGCCP VEGF165      FLQHNKCECRPKK.....DRA.......
SOM175Long   LEEHSQCECRPKKKDSAVKPDRAATPHH VEGF165      GPCSERRKHLFVQDPQTCKCSCKNTDS.
SOM175Long   PRCTQHHQR...PQPRTCRCRCRRRSFL
```

Areas of 100% homology are boxed and conserved residues thought to be involved in homodimerisation are underlined. The VEGF sequence depicted includes the 26 amino acid leader sequence (removal of which gives rise to mature $VEGF_{165}$) giving a total length of 191 amino acids.

Homology of SOM175 to $VEGF_{165}$ is 27% (33%) at the protein level, however within this are blocks of 100% homology. In particular, many structural residues are conserved including those thought to be involved in homodimerisation of VEGF (by comparison with PDGF).
ie.  Cysteine-47
     Proline-70, Cysteine-72, Valine-74
Arginine-77, Cystein-78, Glycine-80, Cysteines-81 & 82
Cysteine-89, Proline-91
Cysteines 122 & 124

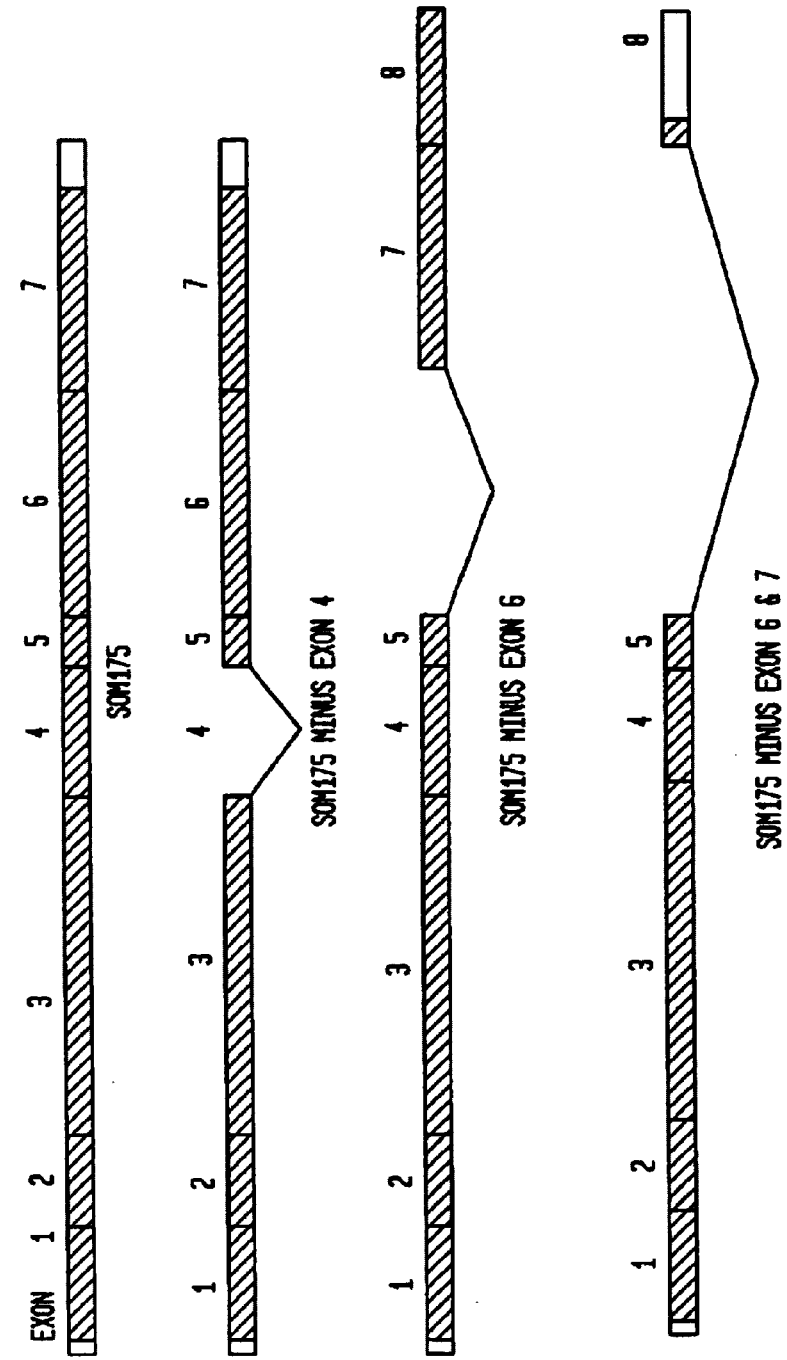

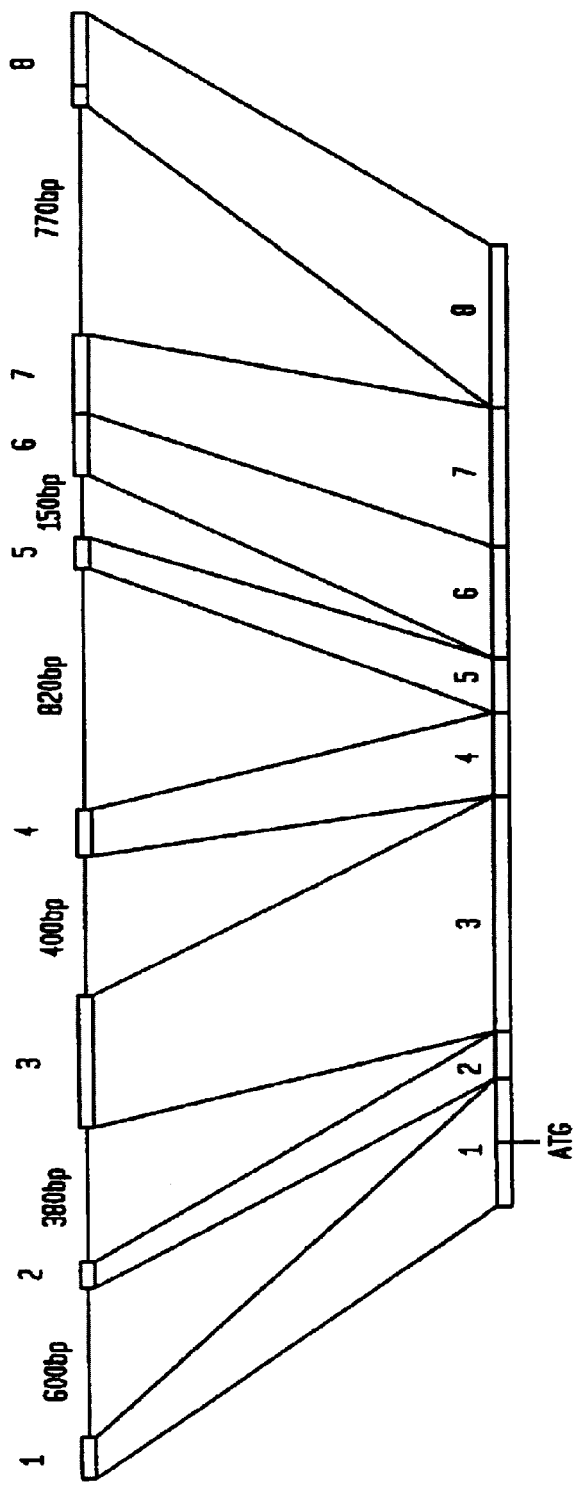

FIG. 8B

```
5'UTR.... ATGAGG *Exon 1  (60bp)   GGCCAG gtacgtgagg
tctcccacag GCCCCT  Exon 2  (43bp)   GGAAAG aatacttaca
tctgctccca TGGTGT  Exon 3  (187bp)  ATGCAG gtccgagatg
ctgaatacag ATCCTC  Exon 4  (73bp)   ATGCAG gtgtcaggca
acttttcaag ACCTAA  Exon 5  (34bp)   AGACAG gtgagtcttt
ctcctccgta GGCTGC  Exon 6  (101bp)  CTCCAG cccaggccc
cccactccag CCCCAG  Exon 7  (109bp)  ACCCAG acacctgtag
ccctgctcag GTGCCG *Exon 8  (22bp)   AGGTGA ...3'UTR
```

FIG. 9A

```
-163   gcacgagctcaggccgtcgctgcggcgctg
-103   ggggccgcggaggagccgcccctgcgcc
 -43   ggcggctctggctgaccccccccacaccg

16   CGTCGCCTGCTGCTTGTTGCACTGCTGCAG
        R  R  L  L  L  V  A  L  L  Q

76   TTTGATGGCCCCAGTCACCAGAAGAAAGTG
        F  D  G  P  S  H  Q  K  K  V

136   ACATGCCAGCCCAGGGAGGTGGTGGTGCCT
        T  C  Q  P  R  E  V  V  V  P

196   AAACAACTAGTGCCCAGCTGTGTGACTGTG
        K  Q  L  V  P  S  C  V  T  V

256   GGCCTGGAATGTGTGCCCACTGGGCAACAC
        G  L  E  C  V  P  T  G  Q  H

316   TACCCGAGCAGTCAGCTGGGGGAGATGTCC
        Y  P  S  S  Q  L  G  E  M  S

376   CCTAAAAAAAAGGAGAGTGCTGTGAGGCCA
        P  K  K  K  E  S  A  V  R  P

436   CAGCCCCGCTCTGTTCCGGGCTGGGACTCT
        Q  P  R  S  V  P  G  W  D  S
```

FIG. 9B

```
cgttgcgctgcctgcgcccagggctcggga
ccgccccgggtccccgggtccgcgccatgg
ccgggctagggcccgATGAGCCCCCTGCTG
                 M  S  P  L  L    -17
                 ↓
CTGGCTCGCACCCAGGCCCCTGTGTCCCAG
 L  A  R  T  Q  A  P  V  S  Q     4

GTGCCATGGATAGACGTTTATGCACGTGCC
 V  P  W  I  D  V  Y  A  R  A    24

CTGAGCATGGAACTCATGGGCAATGTGGTC
 L  S  M  E  L  M  G  N  V  V    44

CAGCGCTGTGGTGGCTGCTGCCCTGACGAT
 Q  R  C  G  G  C  C  P  D  D    64
              ↓
CAAGTCCGAATGCAGATCCTCATGATCCAG
 Q  V  R  M  Q  I  L  M  I  Q    84
                             ↓
CTGGGAGAACACAGCCAATGTGAATGCAGA
 L  G  E  H  S  Q  C  E  C  R   104
 ↓
GACAGGGTTGCCATACCCCACCACCGTCCC
 D  R  V  A  I  P  H  H  R  P   124

ACCCCGGGAGCACCCTCCCCAGCTGACATC
 T  P  G  A  P  S  P  A  D  I   144
```

FIG. 9C

```
496  ATCCATCCCACTCCAGCCCCAGGATCCTCT
      I  H  P  T  P  A  P  G  S  S
                     S  P  R  I  L

556  CTGACCCCCGGACCTGCCGTTGCCGCTGTA
      L  T  P  G  P  A  V  A  A  V
      P  D  P  R  T  C  R  C  R  C

616  GGGGCTTAGAGCTCAACCCAGACACCTGTA
      G  A  *
      R  G  L  E  L  N  P  D  T  C 676  ctttccagactccacgggcccggctgcttt
736  agcacaggcgtaacctcctcagtctgggag
796  gagctctctcgccatcttttatctcccaga
856  atgtctcacctcaggggccagggtactctc
916  ttctggctggctgtctccctcactatgaa
976  gggttctgttatgataactgtgacacacac
1036 gacactaaaaaaaaaaaaaaaaaaaaaaaa
```

FIG. 9D

```
GCCCGCCTTGCACCCAGCGCCGCCAACGCC
 A  R  L  A  P  S  A  A  N  A      164
 C  P  P  C  T  Q  R  R  Q  R      130

GACGCCGCCGCTTCCTCCATTGCCAAGGGC
 D  A  A  A  S  S  I  A  K  G      184
 R  R  R  R  F  L  H  C  Q  G      150
 ↓
GGTGCCGGAAGCCGCGAAAGTGAcaagctg
                                   186
 R  C  R  K  P  R  K  *            167 tatggccctgcttcacagggagaagagtgg
gtcactgccccaggacctggaccttttaga
gctgccatctaacaattgtcaaggaacctc
tcacttaaccaccctggtcaagtgagcatc
aaccccaaacttctaccaataacgggattt
acacactcacactctgataaaagagatgga
aaaaaaaaaaaa
```

| | | |
|---|---|---|
| hVRF167 | -21 | MSPLLRRLLLAALLQLAPAQAP |
| mVRF167 | -21 | MSPLLRRLLLVALLQLARTQAP |
| hVRF167 | 30 | EVVVPLTVELMGTVAKQLVPSC |
| mVRF167 | 30 | EVVVPLSMELMGNVVKQLVPSC |
| hVRF167 | 80 | ILMIRYPSSQLGEMSLEEHSQC |
| mVRF167 | 80 | ILMIQYPSSQLGEMSLGEHSQC |
| hVRF167 | 130 | RPDPRTCRCRCRRRSFLRCQGR |
| mVRF167 | 130 | RPDPRTCRCRCRRRRFLHCQGR |

B

| | | |
|---|---|---|
| hVRF186 | 116 | RAATPHHRPQPRSVPGWDSAPG |
| mVRF186 | 116 | RVAIPHHRPQPRSVPGWDSTPG |
| hVRF186 | 166 | TPGPAAAAADAAASSVAKGGA* |
| mVRF186 | 166 | TPGPAVAAVDAAASSIAKGGA* |

FIG. 10B

```
VSQPDAPGHQRKVVSWIDVYTRATCQPR    29
||| |:|:||:||| ||||| |||||||
VSQFDGPSHQKKVVPWIDVYARATCQPR    29

YTVQRCGGCPDDGLECVPTGQHQVRMQ     79
|||||||||||||||||||||||||||
VTVQRCGGCPDDGLECVPTGQHQVRMQ     79

ECRPKKKDSAVKPDSPRPLCPRCTQHHQ    129
||||||:|||:|||| ||| |||::|
ECRPKKKESAVRPDSPRILCPPCTQRRQ    129

GLELNPDTCRCRKLRR*  167
|||||||||||||||:
GLELNPDTCRCRKPRK*  167

APSPADITHPTPAPGPSAHAAPSTTSAL    165
||||||| ||||||  |:  ||| ||
APSPADIIHPTPAPGSSARLAPSAANAL    165

```
mVRF167   -21   MSPLLRRL..LLVALLQL..
                |  ||  ::   |:  ||  |
mVEGF188  -26   MNFLLSWVHWTLALLLYLHH mVRF167    25   TCQPREVVVPLSMELMGNVV
                |  |  |  :|  :   |    :::
mVEGF188   24   YCRPIETLVDIFQEYPDEIE mVRF167    75   QVRMQILMIQYPSSQ.LGEM
                :  |||:  |       ||  :|||
mVEGF188   74   NITMQIMRIKPHQSQHIGEM mVRF167   119   ...............ILCPPC
                                :  |  ||
mVEGF188  124   QKRKRKKSRFKSWSVHCEPC mVRF167   152   GLELNPDTCRCRKPRK
                ||||  ||||  |||:
mVEGF188  173   QLELNERTCRCDKPRR
```

FIG. 11B

```
       ↓
AR.TQAPVSQFDGPSHQKKVVPWIDVYARA    24
|:  ||:     :|  : ::  |: ::|||| |
AKWSQAAPTT.EGEQKSHEVIKFMDVYQRS    23

KQLVPSCVTVQRCGGCCPDDGLECVPTGQH    74
 : ||||  : ||:|||  |::||||| ::
YIFKPSCVPLMRCAGCCNDEALECVPTSES    73

SLGEHSQCECRPKKKESAVRPDSPR.....   118
|: :||  ||||||||       || ||
SFLQHSRCECRPKKDRTKPEKKSVRGKGKG   123

TQRRQR...PDPRTCRCRCRRRRFLHCQGR   151
 :|| :    || ||:| |:     :| :|
SERRKHLFVQDPQTCKCSCKNTDS.RCKAR   172

167

188
```

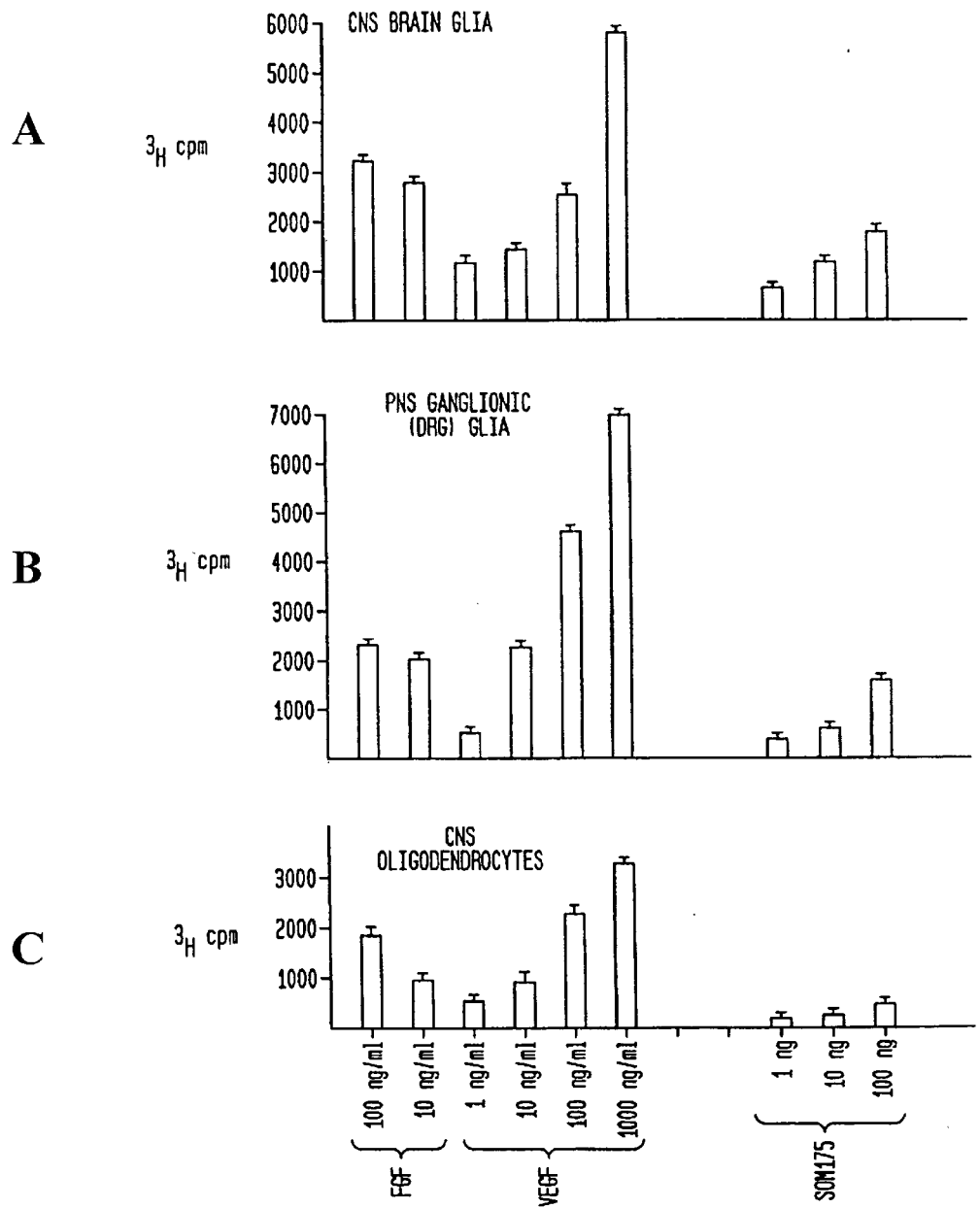

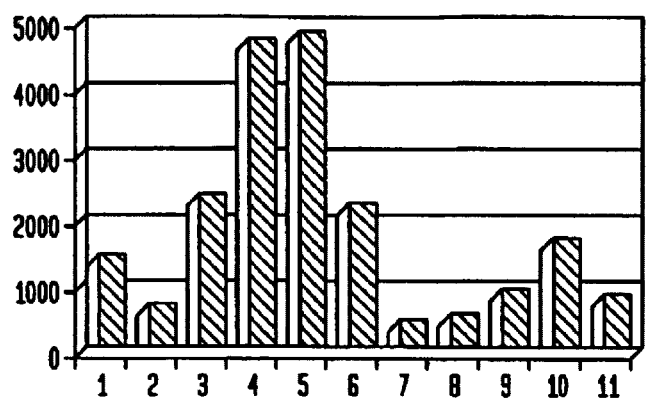
FIG. 15 MOUSE ASTROGLIAL CELLS
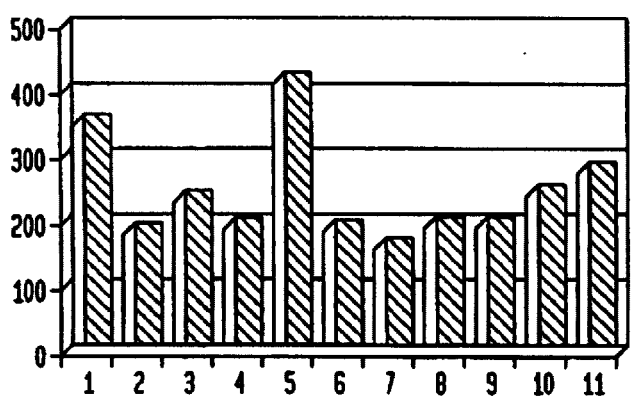
FIG. 16 MOUSE OLIGODENDROGLIAL CELLS
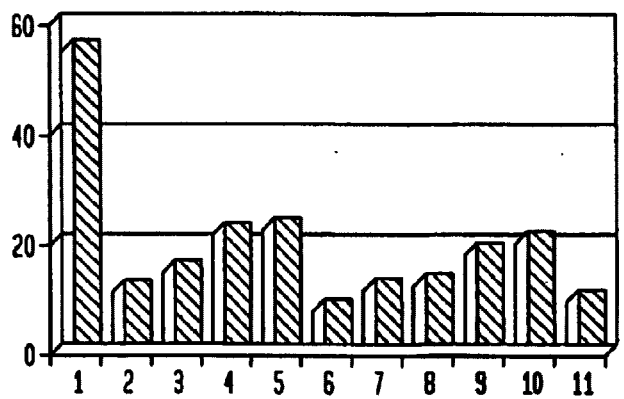
FIG. 17 MOUSE FOREBRAIN NUERONS

SEQUENCE LISTING

```
<160> NUMBER OF SEQ ID NOS: 22

<210> SEQ ID NO 1
<211> LENGTH: 649
<212> TYPE: DNA
<213> ORGANISM: Unknown
<220> FEATURE:
<221> NAME/KEY: CDS
<222> LOCATION: (17)..(589)
<220> FEATURE:
<223> OTHER INFORMATION: Description of Unknown Organism: Nucleotide
      Sequence of VEGF165

<400> SEQUENCE: 1
```

```
tcgggcctcc gaaacc atg aac ttt ctg ctg tct tgg gtg cat tgg agc ctt    52
               Met Asn Phe Leu Leu Ser Trp Val His Trp Ser Leu
                 1               5                  10 gcc ttg ctg ctc tac ctc cac cat gcc aag tgg tcc cag gct gca ccc     100
Ala Leu Leu Leu Tyr Leu His His Ala Lys Trp Ser Gln Ala Ala Pro
         15                  20                  25 atg gca gaa gga gga ggg cag aat cat cac gaa gtg gtg aag ttc atg    148
Met Ala Glu Gly Gly Gly Gln Asn His His Glu Val Val Lys Phe Met
     30                  35                  40 gat gtc tat cag cgc agc tac tgc cat cca atc gag acc ctg gtg gac    196
Asp Val Tyr Gln Arg Ser Tyr Cys His Pro Ile Glu Thr Leu Val Asp
 45                  50                  55                  60 atc ttc cag gag tac cct gat gag atc gag tac atc ttc aag cca tcc    244
Ile Phe Gln Glu Tyr Pro Asp Glu Ile Glu Tyr Ile Phe Lys Pro Ser
                 65                  70                  75 tgt gtg ccc ctg atg cga tgc ggg ggc tgc tgc aat gac gag ggc ctg    292
Cys Val Pro Leu Met Arg Cys Gly Gly Cys Cys Asn Asp Glu Gly Leu
         80                  85                  90 gag tgt gtg ccc act gag gag tcc aac atc acc atg cag att atg cgg    340
Glu Cys Val Pro Thr Glu Glu Ser Asn Ile Thr Met Gln Ile Met Arg
     95                 100                 105 atc aaa cct cac caa ggc cag cac ata gga gag atg agc ttc cta cag    388
Ile Lys Pro His Gln Gly Gln His Ile Gly Glu Met Ser Phe Leu Gln
110                 115                 120 cac aac aaa tgt gaa tgc aga cca aag aaa gat aga gca aga caa gaa    436
His Asn Lys Cys Glu Cys Arg Pro Lys Lys Asp Arg Ala Arg Gln Glu
125                 130                 135                 140 aat ccc tgt ggg cct tgc tca gag cgg aga aag cat ttg ttt gta caa    484
Asn Pro Cys Gly Pro Cys Ser Glu Arg Arg Lys His Leu Phe Val Gln
                145                 150                 155 gat ccg cag acg tgt aaa tgt tcc tgc aaa aac aca gac tcg cgt tgc    532
Asp Pro Gln Thr Cys Lys Cys Ser Cys Lys Asn Thr Asp Ser Arg Cys
            160                 165                 170 aag gcg agg cag ctt gag tta aac gaa cgt act tgc aga tgt gac aag    580
Lys Ala Arg Gln Leu Glu Leu Asn Glu Arg Thr Cys Arg Cys Asp Lys
        175                 180                 185 ccg agg cgg tgagccgggc aggaggaagg agcctccctc agcgtttcgg            629
Pro Arg Arg
    190 gaaccagatc tctcaccagg                                              649
```

```
<210> SEQ ID NO 2
<211> LENGTH: 191
<212> TYPE: PRT
<213> ORGANISM: Unknown
<220> FEATURE:
<223> OTHER INFORMATION: Description of Unknown Organism: Amino Acid
```

Sequence of VEGF165

<400> SEQUENCE: 2

```
Met Asn Phe Leu Leu Ser Trp Val His Trp Ser Leu Ala Leu Leu Leu
 1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```

<210> SEQ ID NO 3
<211> LENGTH: 1094
<212> TYPE: DNA
<213> ORGANISM: Unknown
<220> FEATURE:
<221> NAME/KEY: CDS
<222> LOCATION: (3)..(623)
<220> FEATURE:
<223> OTHER INFORMATION: Description of Unknown Organism:Nucleotide
  Sequence of SOM175

<400> SEQUENCE: 3

```
cc atg agc cct ctg ctc cgc cgc ctg ctg ctc gcc gca ctc ctg cag        47
   Met Ser Pro Leu Leu Arg Arg Leu Leu Leu Ala Ala Leu Leu Gln
    1               5                   10                  15 ctg gcc ccc gcc cag gcc cct gtc tcc cag cct gat gcc cct ggc cac        95
Leu Ala Pro Ala Gln Ala Pro Val Ser Gln Pro Asp Ala Pro Gly His
            20                  25                  30 cag agg aaa gtg gtg tca tgg ata gat gtg tat act cgc gct acc tgc       143
Gln Arg Lys Val Val Ser Trp Ile Asp Val Tyr Thr Arg Ala Thr Cys
        35                  40                  45 cag ccc cgg gag gtg gtg gtg ccc ttg act gtg gag ctc atg ggc acc       191
Gln Pro Arg Glu Val Val Val Pro Leu Thr Val Glu Leu Met Gly Thr
    50                  55                  60 gtg gcc aaa cag ctg gtg ccc agc tgc gtg act gtg cag cgc tgt ggt       239
Val Ala Lys Gln Leu Val Pro Ser Cys Val Thr Val Gln Arg Cys Gly
65                  70                  75 ggc tgc tgc cct gac gat ggc ctg gag tgt gtg ccc act ggg cag cac       287
Gly Cys Cys Pro Asp Asp Gly Leu Glu Cys Val Pro Thr Gly Gln His
        80                  85                  90                  95 caa gtc cgg atg cag atc ctc atg atc cgg tac ccg agc agt cag ctg       335
```

-continued

```
                Gln Val Arg Met Gln Ile Leu Met Ile Arg Tyr Pro Ser Ser Gln Leu
                                100                 105                 110 ggg gag atg tcc ctg gaa gaa cac agc cag tgt gaa tgc aga cct aaa       383
Gly Glu Met Ser Leu Glu Glu His Ser Gln Cys Glu Cys Arg Pro Lys
            115                 120                 125 aaa aag gac agt gct gtg aag cca gac agg gct gcc act ccc cac cac       431
Lys Lys Asp Ser Ala Val Lys Pro Asp Arg Ala Ala Thr Pro His His
        130                 135                 140 cgt ccc cag ccc cgt tct gtt ccg ggc tgg gac tct gcc ccc gga gca       479
Arg Pro Gln Pro Arg Ser Val Pro Gly Trp Asp Ser Ala Pro Gly Ala
    145                 150                 155 ccc tcc cca gct gac atc acc cat ccc act cca gcc cca ggc ccc tct       527
Pro Ser Pro Ala Asp Ile Thr His Pro Thr Pro Ala Pro Gly Pro Ser
160                 165                 170                 175 gcc cac gct gca ccc agc acc acc agc gcc ctg acc ccc gga cct gcc       575
Ala His Ala Ala Pro Ser Thr Thr Ser Ala Leu Thr Pro Gly Pro Ala
                180                 185                 190 gct gcc gct gcc gac gcc gca gct tcc tcc gtt gcc aag ggc ggg gct       623
Ala Ala Ala Ala Asp Ala Ala Ala Ser Ser Val Ala Lys Gly Gly Ala
            195                 200                 205 tagagctcaa cccagacacc tgcaggtgcc ggaagctgcg aaggtgacac atggcttttc     683
agactcagca gggtgacttg cctcagaggc tatatcccag tgggggaaca aaggggagcc     743
tggtaaaaaa cagccaagcc cccaagacct cagcccaggc agaagctgct ctaggacctg     803
ggcctctcag agggctcttc tgccatccct tgtctccctg aggccatcat caaacaggac     863
agagttggaa gaggagactg ggaggcagca agagggtca catccagct caggggagaa       923 tggagtactg tctcagtttc taaccactct gtgcaagtaa gcatcttaca actggctctt     983
cctcccctca ctaagaagac ccaaacctct gcataatggg atttgggctt tggtacaaga    1043
actgtgaccc ccaaccctga taaagagat ggaaggaaaa aaaaaaaaa a               1094
```

<210> SEQ ID NO 4
<211> LENGTH: 207
<212> TYPE: PRT
<213> ORGANISM: Unknown
<220> FEATURE:
<223> OTHER INFORMATION: Description of Unknown Organism: Amino Acid
      Sequence of SOM175

<400> SEQUENCE: 4

```
Met Ser Pro Leu Leu Arg Arg Leu Leu Leu Ala Ala Leu Leu Gln Leu
 1               5                  10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Arg Ala Ala Thr Pro His His Arg
```

```
              130                 135                 140
Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
        195                 200                 205

<210> SEQ ID NO 5
<211> LENGTH: 993
<212> TYPE: DNA
<213> ORGANISM: Unknown
<220> FEATURE:
<221> NAME/KEY: CDS
<222> LOCATION: (3)..(566)
<220> FEATURE:
<223> OTHER INFORMATION: Description of Unknown Organism:Nucleotide
      Sequence of SOM175 Absent Exon 6

<400> SEQUENCE: 5
```

| | | |
|---|---|---|
| cc atg agc cct ctg ctc cgc cgc ctg ctg ctc gcc gca ctc ctg cag<br>   Met Ser Pro Leu Leu Arg Arg Leu Leu Leu Ala Ala Leu Leu Gln<br>      1             5                 10                15 | 47 |
| ctg gcc ccc gcc cag gcc cct gtc tcc cag cct gat gcc cct ggc cac<br>Leu Ala Pro Ala Gln Ala Pro Val Ser Gln Pro Asp Ala Pro Gly His<br>                20                25                30 | 95 |
| cag agg aaa gtg gtg tca tgg ata gat gtg tat act cgc gct acc tgc<br>Gln Arg Lys Val Val Ser Trp Ile Asp Val Tyr Thr Arg Ala Thr Cys<br>              35                40                45 | 143 |
| cag ccc cgg gag gtg gtg gtg ccc ttg act gtg gag ctc atg ggc acc<br>Gln Pro Arg Glu Val Val Val Pro Leu Thr Val Glu Leu Met Gly Thr<br>      50                55                60 | 191 |
| gtg gcc aaa cag ctg gtg ccc agc tgc gtg act gtg cag cgc tgt ggt<br>Val Ala Lys Gln Leu Val Pro Ser Cys Val Thr Val Gln Arg Cys Gly<br> 65                70                75 | 239 |
| ggc tgc tgc cct gac gat ggc ctg gag tgt gtg ccc act ggg cag cac<br>Gly Cys Cys Pro Asp Asp Gly Leu Glu Cys Val Pro Thr Gly Gln His<br>80                85                90              95 | 287 |
| caa gtc cgg atg cag atc ctc atg atc cgg tac ccg agc agt cag ctg<br>Gln Val Arg Met Gln Ile Leu Met Ile Arg Tyr Pro Ser Ser Gln Leu<br>                100              105            110 | 335 |
| ggg gag atg tcc ctg gaa gaa cac agc cag tgt gaa tgc aga cct aaa<br>Gly Glu Met Ser Leu Glu Glu His Ser Gln Cys Glu Cys Arg Pro Lys<br>         115                120              125 | 383 |
| aaa aag gac agt gct gtg aag cca gat agc ccc agg ccc ctc tgc cca<br>Lys Lys Asp Ser Ala Val Lys Pro Asp Ser Pro Arg Pro Leu Cys Pro<br>     130               135              140 | 431 |
| cgc tgc acc cag cac cac cag cgc cct gac ccc cgg acc tgc cgc tgc<br>Arg Cys Thr Gln His His Gln Arg Pro Asp Pro Arg Thr Cys Arg Cys<br>145                150                155 | 479 |
| cgc tgc cga cgc cgc agc ttc ctc cgt tgc caa ggg cgg ggc tta gag<br>Arg Cys Arg Arg Arg Ser Phe Leu Arg Cys Gln Gly Arg Gly Leu Glu<br>160                165              170            175 | 527 |
| ctc aac cca gac acc tgc agg tgc cgg aag ctg cga agg tgacacatgg<br>Leu Asn Pro Asp Thr Cys Arg Cys Arg Lys Leu Arg Arg<br>         180                185 | 576 |
| cttttcagac tcagcagggt gacttgcctc agaggctata tcccagtggg ggaacaaagg | 636 |
| ggagcctggt aaaaaacagc caagccccca agacctcagc ccaggcagaa gctgctctag | 696 |

-continued

```
gacctgggcc tctcagaggg ctcttctgcc atcccttgtc tccctgaggc catcatcaaa      756
caggacagag ttggaagagg agactgggag gcagcaagag gggtcacata ccagctcagg      816
ggagaatgga gtactgtctc agtttctaac cactctgtgc aagtaagcat cttacaactg      876
gctcttcctc ccctcactaa gaagacccaa acctctgcat aatgggattt gggctttggt      936
acaagaactg tgaccccaa ccctgataaa agagatggaa ggaaaaaaaa aaaaaaa         993
```

<210> SEQ ID NO 6
<211> LENGTH: 188
<212> TYPE: PRT
<213> ORGANISM: Unknown
<220> FEATURE:
<223> OTHER INFORMATION: Description of Unknown Organism: Amino Acid
      Sequence of SOM175 Absent Exon 6

<400> SEQUENCE: 6

```
Met Ser Pro Leu Leu Arg Arg Leu Leu Leu Ala Ala Leu Leu Gln Leu
  1               5                  10                  15

Ala Pro Ala Gln Ala Pro Val Ser Gln Pro Asp Ala Pro Gly His Gln
             20                  25                  30

Arg Lys Val Val Ser Trp Ile Asp Val Tyr Thr Arg Ala Thr Cys Gln
         35                  40                  45

Pro Arg Glu Val Val Val Pro Leu Thr Val Glu Leu Met Gly Thr Val
     50                  55                  60

Ala Lys Gln Leu Val Pro Ser Cys Val Thr Val Gln Arg Cys Gly Gly
 65                  70                  75                  80

Cys Cys Pro Asp Asp Gly Leu Glu Cys Val Pro Thr Gly Gln His Gln
                 85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Ser Pro Arg Pro Leu Cys Pro Arg
    130                 135                 140

Cys Thr Gln His His Gln Arg Pro Asp Pro Arg Thr Cys Arg Cys Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
            180                 185
```

<210> SEQ ID NO 7
<211> LENGTH: 858
<212> TYPE: DNA
<213> ORGANISM: Unknown
<220> FEATURE:
<221> NAME/KEY: CDS
<222> LOCATION: (3)..(431)
<220> FEATURE:
<223> OTHER INFORMATION: Description of Unknown Organism:Nucleotide
      Sequence of SOM175 Absent Exons 6 & 7

<400> SEQUENCE: 7

```
cc atg agc cct ctg ctc cgc cgc ctg ctg ctc gcc gca ctc ctg cag      47
   Met Ser Pro Leu Leu Arg Arg Leu Leu Leu Ala Ala Leu Leu Gln
     1               5                  10                  15 ctg gcc ccc gcc cag gcc cct gtc tcc cag cct gat gcc cct ggc cac      95
Leu Ala Pro Ala Gln Ala Pro Val Ser Gln Pro Asp Ala Pro Gly His
             20                  25                  30
```

```
cag agg aaa gtg gtg tca tgg ata gat gtg tat act cgc gct acc tgc     143
Gln Arg Lys Val Val Ser Trp Ile Asp Val Tyr Thr Arg Ala Thr Cys
            35                  40                  45 cag ccc cgg gag gtg gtg gtg ccc ttg act gtg gag ctc atg ggc acc     191
Gln Pro Arg Glu Val Val Val Pro Leu Thr Val Glu Leu Met Gly Thr
 50                  55                  60 gtg gcc aaa cag ctg gtg ccc agc tgc gtg act gtg cag cgc tgt ggt     239
Val Ala Lys Gln Leu Val Pro Ser Cys Val Thr Val Gln Arg Cys Gly
         65                  70                  75 ggc tgc tgc cct gac gat ggc ctg gag tgt gtg ccc act ggg cag cac     287
Gly Cys Cys Pro Asp Asp Gly Leu Glu Cys Val Pro Thr Gly Gln His
 80                  85                  90                  95 caa gtc cgg atg cag atc ctc atg atc cgg tac ccg agc agt cag ctg     335
Gln Val Arg Met Gln Ile Leu Met Ile Arg Tyr Pro Ser Ser Gln Leu
                100                 105                 110 ggg gag atg tcc ctg gaa gaa cac agc cag tgt gaa tgc aga cct aaa     383
Gly Glu Met Ser Leu Glu Glu His Ser Gln Cys Glu Cys Arg Pro Lys
            115                 120                 125 aaa aag gac agt gct gtg aag cca gat agg tgc cgg aag ctg cga agg     431
Lys Lys Asp Ser Ala Val Lys Pro Asp Arg Cys Arg Lys Leu Arg Arg
        130                 135                 140 tgacacatgg cttttcagac tcagcagggt gacttgcctc agaggctata tcccagtggg   491
ggaacaaagg ggagcctggt aaaaaacagc caagccccca agacctcagc ccaggcagaa   551
gctgctctag gacctgggcc tctcagaggg ctcttctgcc atcccttgtc tccctgaggc   611
catcatcaaa caggacagag ttggaagagg agactgggag gcagcaagag gggtcacata   671
ccagctcagg ggagaatgga gtactgtctc agtttctaac cactctgtgc aagtaagcat   731
cttacaactg gctcttcctc ccctcactaa gaagacccaa acctctgcat aatgggattt   791
gggctttggt acaagaactg tgacccccaa ccctgataaa agagatggaa ggaaaaaaaa   851
aaaaaaa                                                             858

<210> SEQ ID NO 8
<211> LENGTH: 143
<212> TYPE: PRT
<213> ORGANISM: Unknown
<220> FEATURE:
<223> OTHER INFORMATION: Description of Unknown Organism: Amino Acid
      Sequence of SOM175 Absent Exons 6 & 7

<400> SEQUENCE: 8

Met Ser Pro Leu Leu Arg Arg Leu Leu Leu Ala Ala Leu Leu Gln Leu
 1               5                  10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125
```

```
       Lys Asp Ser Ala Val Lys Pro Asp Arg Cys Arg Lys Leu Arg Arg
           130                 135                 140

<210> SEQ ID NO 9
<211> LENGTH: 910
<212> TYPE: DNA
<213> ORGANISM: Unknown
<220> FEATURE:
<221> NAME/KEY: CDS
<222> LOCATION: (3)..(305)
<220> FEATURE:
<223> OTHER INFORMATION: Description of Unknown Organism:Nucleotide
      Sequence of SOM175 Absent Exon 4

<400> SEQUENCE: 9 cc atg agc cct ctg ctc cgc cgc ctg ctg ctc gcc gca ctc ctg cag          47
   Met Ser Pro Leu Leu Arg Arg Leu Leu Leu Ala Ala Leu Leu Gln
     1               5                  10                  15 ctg gcc ccc gcc cag gcc cct gtc tcc cag cct gat gcc cct ggc cac         95
Leu Ala Pro Ala Gln Ala Pro Val Ser Gln Pro Asp Ala Pro Gly His
             20                  25                  30 cag agg aaa gtg gtg tca tgg ata gat gtg tat act cgc gct acc tgc        143
Gln Arg Lys Val Val Ser Trp Ile Asp Val Tyr Thr Arg Ala Thr Cys
 35                  40                  45 cag ccc cgg gag gtg gtg gtg ccc ttg act gtg gag ctc atg ggc acc        191
Gln Pro Arg Glu Val Val Val Pro Leu Thr Val Glu Leu Met Gly Thr
     50                  55                  60 gtg gcc aaa cag ctg gtg ccc agc tgc gtg act gtg cag cgc tgt ggt        239
Val Ala Lys Gln Leu Val Pro Ser Cys Val Thr Val Gln Arg Cys Gly
 65                  70                  75 ggc tgc tgc cct gac gat ggc ctg gag tgt gtg ccc act ggg cag cac        287
Gly Cys Cys Pro Asp Asp Gly Leu Glu Cys Val Pro Thr Gly Gln His
 80                  85                  90                  95 caa gtc cgg atg cag acc taaaaaaaag gacagtgctg tgaagccaga               335
Gln Val Arg Met Gln Thr
                100 cagggctgcc actccccacc accgtcccca gccccgttct gttccgggct gggactctgc      395 ccccggagca ccctccccag ctgacatcac ccatcccact ccagcccag gcccctctgc       455 ccacgctgca cccagcacca ccagcgccct gaccccgga cctgccgctg ccgctgccga       515 cgccgcagct tcctccgttg ccaagggcgg ggcttagagc tcaacccaga cacctgcagg      575 tgccggaagc tgcgaaggtg acacatggct tttcagactc agcagggtga cttgcctcag      635 aggctatatc ccagtgggga acaaagagga gcctggtaaa aaacagccaa gccccaaga      695 cctcagccca ggcagaagct gctctaggac ctgggcctct cagagggctc ttctgccatc      755 ccttgtctcc ctgaggccat catcaaacag gacagagttg gaagaggaga ctgggaggca      815 gcaagagggg tcacatacca gctcagggga gaatggagta ctgtctcagt ttctaaccac      875 tctgtgcaag taagcatctt acaactggct cttcc                                 910

<210> SEQ ID NO 10
<211> LENGTH: 101
<212> TYPE: PRT
<213> ORGANISM: Unknown
<220> FEATURE:
<223> OTHER INFORMATION: Description of Unknown Organism: Amino Acid
      Sequence of SOM175 Absent Exon 4

<400> SEQUENCE: 10

Met Ser Pro Leu Leu Arg Arg Leu Leu Leu Ala Ala Leu Leu Gln Leu
  1               5                  10                  15
```

```
Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Thr
            100
```

```
<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide complementary to nt 120-161

<400> SEQUENCE: 11
accaccacct ccctgggctg gcatgtggca cgtgcataaa cg                42
```

```
<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide complementary to nt 162-203

<400> SEQUENCE: 12
agttgtttga ccacattgcc catgagttcc atgctcagag gc                42
```

```
<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide complementary to mRNA encoding in mVRF

<400> SEQUENCE: 13
gatcctgggg ctggagtggg atggatgatg tcagctgg                    38
```

```
<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide complementary to mRNA encoding mVRF

<400> SEQUENCE: 14
gcgggcagag gatcctgggg ctgtctggcc tcacagcact                   40
```

```
<210> SEQ ID NO 15
<211> LENGTH: 236
<212> TYPE: DNA
<213> ORGANISM: Unknown
<220> FEATURE:
<223> OTHER INFORMATION: Description of Unknown Organism:Human SOM175
```

-continued

```
<400> SEQUENCE: 15
atgaggggcc aggtacgtga ggtctcccac aggcccctgg aaagaatact tacatctgct      60
cccatggtgt atgcaggtcc gagatgctga atacagatcc tcatgcaggt gtcaggcaac     120
ttttcaagac ctaaagacag gtgagtcttt ctcctccgta ggctgcctcc agccccaggc     180
cccccactcc agcccagac ccagacacct gtagccctgc tcaggtgccg aggtga          236

<210> SEQ ID NO 16
<211> LENGTH: 1242
<212> TYPE: DNA
<213> ORGANISM: Unknown
<220> FEATURE:
<221> NAME/KEY: CDS
<222> LOCATION: (166)..(789)
<220> FEATURE:
<223> OTHER INFORMATION: Description of Unknown Organism:mVRF

<400> SEQUENCE: 16
gcacgagctc aggccgtcgc tgcggcgctg cgttgcgctg cctgcgccca gggctcggga      60 ggggccgcg gaggagccgc ccctgcgcc ccgccccggg tccccgggtc cgcgccatgg      120
ggcggctctg gctgaccccc ccccacaccg ccgggctagg gcccg atg agc ccc ctg     177
                                                 Met Ser Pro Leu
                                                  1 ctg cgt cgc ctg ctg ctt gtt gca ctg ctg cag ctg gct cgc acc cag       225
Leu Arg Arg Leu Leu Leu Val Ala Leu Leu Gln Leu Ala Arg Thr Gln
  5                  10                  15                  20 gcc cct gtg tcc cag ttt gat ggc ccc agt cac cag aag aaa gtg gtg       273
Ala Pro Val Ser Gln Phe Asp Gly Pro Ser His Gln Lys Lys Val Val
             25                  30                  35 cca tgg ata gac gtt tat gca cgt gcc aca tgc cag ccc agg gag gtg       321
Pro Trp Ile Asp Val Tyr Ala Arg Ala Thr Cys Gln Pro Arg Glu Val
         40                  45                  50 gtg gtg cct ctg agc atg gaa ctc atg ggc aat gtg gtc aaa caa cta       369
Val Val Pro Leu Ser Met Glu Leu Met Gly Asn Val Val Lys Gln Leu
     55                  60                  65 gtg ccc agc tgt gtg act gtg cag cgc tgt ggt ggc tgc tgc cct gac       417
Val Pro Ser Cys Val Thr Val Gln Arg Cys Gly Gly Cys Cys Pro Asp
 70                  75                  80 gat ggc ctg gaa tgt gtg ccc act ggg caa cac caa gtc cga atg cag       465
Asp Gly Leu Glu Cys Val Pro Thr Gly Gln His Gln Val Arg Met Gln
 85                  90                  95                 100 atc ctc atg atc cag tac ccg agc agt cag ctg ggg gag atg tcc ctg       513
Ile Leu Met Ile Gln Tyr Pro Ser Ser Gln Leu Gly Glu Met Ser Leu
                105                 110                 115 gga gaa cac agc caa tgt gaa tgc aga cct aaa aaa aag gag agt gct       561
Gly Glu His Ser Gln Cys Glu Cys Arg Pro Lys Lys Lys Glu Ser Ala
            120                 125                 130 gtg agg cca gac agg gtt gcc ata ccc cac cac cgt ccc cag ccc cgc       609
Val Arg Pro Asp Arg Val Ala Ile Pro His His Arg Pro Gln Pro Arg
        135                 140                 145 tct gtt ccg ggc tgg gac tct acc ccg gga gca ccc tcc cca gct gac       657
Ser Val Pro Gly Trp Asp Ser Thr Pro Gly Ala Pro Ser Pro Ala Asp
    150                 155                 160 atc atc cat ccc act cca gcc cca gga tcc tct gcc cgc ctt gca ccc       705
Ile Ile His Pro Thr Pro Ala Pro Gly Ser Ser Ala Arg Leu Ala Pro
165                 170                 175                 180 agc gcc gcc aac gcc ctg acc ccc gga cct gcc gtt gcc gct gta gac       753
Ser Ala Ala Asn Ala Leu Thr Pro Gly Pro Ala Val Ala Ala Val Asp
                185                 190                 195
```

-continued

```
gcc gcc gct tcc tcc att gcc aag ggc ggg gct tag agctcaaccc            799
Ala Ala Ala Ser Ser Ile Ala Lys Gly Gly Ala
            200                 205 agacacctgt aggtgccgga agccgcgaaa gtgacaagct gctttccaga ctccacgggc    859
ccggctgctt ttatggccct gcttcacagg gagaagagtg gagcacaggc gtaacctcct    919
cagtctggga ggtcactgcc ccaggacctg gacctttttag agagctctct cgccatcttt   979
tatctcccag agctgccatc taacaattgt caaggaacct catgtctcac ctcagggcc    1039 agggtactct ctcacttaac caccctggtc aagtgagcat cttctggctg gctgtctccc   1099
ctcactatga aaaccccaaa cttctaccaa taacgggatt tgggttctgt tatgataact   1159
gtgacacaca cacacactca cactctgata aagagatgg agacactaaa aaaaaaaaa    1219 aaaaaaaaaa aaaaaaaaaa aaa                                           1242
```

<210> SEQ ID NO 17
<211> LENGTH: 207
<212> TYPE: PRT
<213> ORGANISM: Unknown
<220> FEATURE:
<223> OTHER INFORMATION: Description of Unknown Organism: Amino Acid
      Sequence of mVRF

<400> SEQUENCE: 17

```
Met Ser Pro Leu Leu Arg Arg Leu Leu Leu Val Ala Leu Leu Gln Leu
 1               5                  10                  15

Ala Arg Thr Gln Ala Pro Val Ser Gln Phe Asp Gly Pro Ser His Gln
            20                  25                  30

Lys Lys Val Val Pro Trp Ile Asp Val Tyr Ala Arg Ala Thr Cys Gln
        35                  40                  45

Pro Arg Glu Val Val Pro Leu Ser Met Glu Leu Met Gly Asn Val
    50                  55                  60

Val Lys Gln Leu Val Pro Ser Cys Val Thr Val Gln Arg Cys Gly Gly
 65                  70                  75                  80

Cys Cys Pro Asp Asp Gly Leu Glu Cys Val Pro Thr Gly Gln His Gln
                85                  90                  95

Val Arg Met Gln Ile Leu Met Ile Gln Tyr Pro Ser Ser Gln Leu Gly
            100                 105                 110

Glu Met Ser Leu Gly Glu His Ser Gln Cys Glu Cys Arg Pro Lys Lys
        115                 120                 125

Lys Glu Ser Ala Val Arg Pro Asp Arg Val Ala Ile Pro His His Arg
    130                 135                 140

Pro Gln Pro Arg Ser Val Pro Gly Trp Asp Ser Thr Pro Gly Ala Pro
145                 150                 155                 160

Ser Pro Ala Asp Ile Ile His Pro Thr Pro Ala Pro Gly Ser Ser Ala
                165                 170                 175

Arg Leu Ala Pro Ser Ala Ala Asn Ala Leu Thr Pro Gly Pro Ala Val
            180                 185                 190

Ala Ala Val Asp Ala Ala Ala Ser Ser Ile Ala Lys Gly Gly Ala
        195                 200                 205
```

<210> SEQ ID NO 18
<211> LENGTH: 188
<212> TYPE: PRT
<213> ORGANISM: Unknown
<220> FEATURE:
<223> OTHER INFORMATION: Description of Unknown Organism:mVRF167

<400> SEQUENCE: 18

-continued

```
Met Ser Pro Leu Leu Arg Arg Leu Leu Leu Val Ala Leu Leu Gln Leu
 1               5                  10                  15

Ala Arg Thr Gln Ala Pro Val Ser Gln Phe Asp Gly Pro Ser His Gln
            20                  25                  30

Lys Lys Val Val Pro Trp Ile Asp Val Tyr Ala Arg Ala Thr Cys Gln
         35                  40                  45

Pro Arg Glu Val Val Pro Leu Ser Met Glu Leu Met Gly Asn Val
 50                  55                  60

Val Lys Gln Leu Val Pro Ser Cys Val Thr Val Gln Arg Cys Gly Gly
 65                  70                  75                  80

Cys Cys Pro Asp Asp Gly Leu Glu Cys Val Pro Thr Gly Gln His Gln
                85                  90                  95

Val Arg Met Gln Ile Leu Met Ile Gln Tyr Pro Ser Ser Gln Leu Gly
                100                 105                 110

Glu Met Ser Leu Gly Glu His Ser Gln Cys Glu Cys Arg Pro Lys Lys
            115                 120                 125

Lys Glu Ser Ala Val Arg Pro Asp Ser Pro Arg Ile Leu Cys Pro Pro
130                 135                 140

Cys Thr Gln Arg Arg Gln Arg Pro Asp Pro Arg Thr Cys Arg Cys Arg
145                 150                 155                 160

Cys Arg Arg Arg Arg Phe Leu His Cys Gln Gly Arg Gly Leu Glu Leu
                165                 170                 175

Asn Pro Asp Thr Cys Arg Cys Arg Lys Pro Arg Lys
                180                 185
```

<210> SEQ ID NO 19
<211> LENGTH: 188
<212> TYPE: PRT
<213> ORGANISM: Unknown
<220> FEATURE:
<223> OTHER INFORMATION: Description of Unknown Organism:hVRF167

<400> SEQUENCE: 19

```
Met Ser Pro Leu Leu Arg Arg Leu Leu Leu Ala Ala Leu Leu Gln Leu
 1               5                  10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
         35                  40                  45

Pro Arg Glu Val Val Pro Leu Thr Val Glu Leu Met Gly Thr Val
 50                  55                  60

Ala Lys Gln Leu Val Pro Ser Cys Val Thr Val Gln Arg Cys Gly Gly
 65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
                100                 105                 110

Glu Met Ser Leu Glu Glu His Ser Gln Cys Glu Cys Arg Pro Lys Lys
            115                 120                 125

Lys Asp Ser Ala Val Lys Pro Asp Ser Pro Arg Pro Leu Cys Pro Arg
130                 135                 140

Cys Thr Gln His His Gln Arg Pro Asp Pro Arg Thr Cys Arg Cys Arg
145                 150                 155                 160

Cys Arg Arg Arg Ser Phe Leu Arg Cys Gln Gly Arg Gly Leu Glu Leu
                165                 170                 175
```

-continued

Asn Pro Asp Thr Cys Arg Cys Arg Lys Leu Arg Arg
            180                 185

<210> SEQ ID NO 20
<211> LENGTH: 71
<212> TYPE: PRT
<213> ORGANISM: Unknown
<220> FEATURE:
<223> OTHER INFORMATION: Description of Unknown Organism:mVRF186

<400> SEQUENCE: 20

Arg Val Ala Ile Pro His His Arg Pro Gln Pro Arg Ser Val Pro Gly
  1               5                  10                  15

Trp Asp Ser Thr Pro Gly Ala Pro Ser Pro Ala Asp Ile Ile His Pro
                 20                  25                  30

Thr Pro Ala Pro Gly Ser Ser Ala Arg Leu Ala Pro Ser Ala Ala Asn
             35                  40                  45

Ala Leu Thr Pro Gly Pro Ala Val Ala Val Asp Ala Ala Ser
         50                  55                  60

Ser Ile Ala Lys Gly Gly Ala
 65                  70

<210> SEQ ID NO 21
<211> LENGTH: 71
<212> TYPE: PRT
<213> ORGANISM: Unknown
<220> FEATURE:
<223> OTHER INFORMATION: Description of Unknown Organism:hVRF186

<400> SEQUENCE: 21

Arg Ala Ala Thr Pro His His Arg Pro Gln Pro Arg Ser Val Pro Gly
  1               5                  10                  15

Trp Asp Ser Ala Pro Gly Ala Pro Ser Pro Ala Asp Ile Thr His Pro
                 20                  25                  30

Thr Pro Ala Pro Gly Pro Ser Ala His Ala Ala Pro Ser Thr Thr Ser
             35                  40                  45

Ala Leu Thr Pro Gly Pro Ala Ala Ala Ala Asp Ala Ala Ser
         50                  55                  60

Ser Val Ala Lys Gly Gly Ala
 65                  70

<210> SEQ ID NO 22
<211> LENGTH: 214
<212> TYPE: PRT
<213> ORGANISM: Unknown
<220> FEATURE:
<223> OTHER INFORMATION: Description of Unknown Organism:mVEGF188

<400> SEQUENCE: 22

Met Asn Phe Leu Leu Ser Trp Val His Trp Thr Leu Ala Leu Leu Leu
  1               5                  10                  15

Tyr Leu His His Ala Lys Trp Ser Gln Ala Ala Pro Thr Thr Glu Gly
                 20                  25                  30

Glu Gln Lys Ser His Glu Val Ile Lys Phe Met Asp Val Tyr Gln Arg
             35                  40                  45

Ser Tyr Cys Arg Pro Ile Glu Thr Leu Val Asp Ile Phe Gln Glu Tyr
         50                  55                  60

Pro Asp Glu Ile Glu Tyr Ile Phe Lys Pro Ser Cys Val Pro Leu Met
 65                  70                  75                  80

-continued

```
Arg Cys Ala Gly Cys Cys Asn Asp Glu Ala Leu Glu Cys Val Pro Thr
            85                  90                  95

Ser Glu Ser Asn Ile Thr Met Gln Ile Met Arg Ile Lys Pro His Gln
            100                 105                 110

Ser Gln His Ile Gly Glu Met Ser Phe Leu Gln His Ser Arg Cys Glu
            115                 120                 125

Cys Arg Pro Lys Lys Asp Arg Thr Lys Pro Glu Lys Lys Ser Val Arg
130                 135                 140

Gly Lys Gly Lys Gly Gln Lys Arg Lys Arg Lys Lys Ser Arg Phe Lys
145                 150                 155                 160

Ser Trp Ser Val His Cys Glu Pro Cys Ser Glu Arg Arg Lys His Leu
            165                 170                 175

Phe Val Gln Asp Pro Gln Thr Cys Lys Cys Ser Cys Lys Asn Thr Asp
            180                 185                 190

Ser Arg Cys Lys Ala Arg Gln Leu Glu Leu Asn Glu Arg Thr Cys Arg
            195                 200                 205

Cys Asp Lys Pro Arg Arg
210
```

VASCULAR ENDOTHELIAL GROWTH FACTOR POLYPEPTIDES

CROSS REFERENCE TO RELATED APPLICATION

The present application is a divisional of application Ser. No. 08/765,588, filed Apr. 25, 1997.

The present invention relates generally to an isolated molecule having vascular endothelial growth factor-like properties and to a genetic sequence encoding same. The molecule will be useful in the development of a range of therapeutics and diagnostics useful in the treatment, prophylaxis and/or diagnosis of conditions requiring enhanced or diminished vasculature and/or vascular permeability. The molecule of the present invention is also a useful effector of primary and central neurons and is capable of inducing astroglial proliferation.

Bibliographic details of the publications referred to by author in this specification are collected at the end of the description. Sequence Identity Numbers (SEQ ID NOs.) for the nucleotide and amino acid sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Vascular endothelial growth factor (hereinafter referred to as "VEGF"), also known as vasoactive permeability factor, is a secreted, covalently linked homodimeric glycoprotein that specifically activates endothelial tissues (Senger et al., 1993). A range of functions have been attributed to VEGF such as its involvement in normal angiogensis including formation of the corpus luteum (Yari et al., 1993) and placental development (Sharkey et al., 1993), regulation of vascular permeability (Senger et al., 1993), inflammatory angiogenesis (Sunderkotter et al., 1994) and autotransplantation (Dissen et al., 1994) and human diseases such as tumour promoting angiogenesis (Folkman & Shing, 1992), rheumatoid arthritis (Koch et al., 1994) and diabetes related retinopathy (Folkman & Shing, 1992).

VEGF is, therefore, an important molecule making it a potentially valuable target for research into therapeutics, prophylactics and diagnostic agents based on VEGF or its activities. There is also a need to identify homologues or otherwise related molecules for use as an alternative to VEGF or in conjunction with VEGF.

In work leading up to the present invention, the inventors sought the multiple endocrine neoplasia type I susceptibility gene (MEN1). Surprisingly, the inventors discovered that a genetic sequence excluded as a candidate for the MEN1 gene was nevertheless a new growth factor having some similarity to VEGF. Furthermore, the growth factor of the present invention is an effector molecule for primary and central neurons.

Accordingly, one aspect of the present invention comprises a biologically isolated proteinaceous molecule comprising a sequence of amino acids which:
  (i) is at least about 15% similar to the amino acid sequence set forth in SEQ ID NO:2; and
  (ii) is at least 5% dissimilar to the amino acid sequence set forth in SEQ ID NO:2.

Another aspect of the present invention provides a biologically isolated proteinaceous molecule having the following characteristics:
  (i) comprises an amino acid sequence having at least about 15% similarity but at least about 5% dissimilarity to all or part of the amino acid sequence set forth in SEQ ID NO:2;
  (ii) exhibits at least one property in common with VEGF.

A related aspect of the present invention contemplates a biologically isolated proteinaceous molecule having the following characteristics:
  (i) comprises an amino acid sequence having at least about 15% similarity but at least about 5% dissimilarity to the amino acid sequence set forth in SEQ ID NO:2;
  (ii) exhibits at least one of the following properties:
    (a) ability to induce proliferation of vascular endothelial cells;
    (b) ability to interact with flt-1/flk-1 family of receptors;
    (c) ability to induce cell migration, cell survival and/or an increase in intracellular levels of alkaline phosphatase.

By "biologically isolated" is meant that the molecule has undergone at least one step of purification from a biological source. Preferably, the molecule is also biologically pure meaning that a composition comprises at least about 20%, more preferably at least about 40%, still more preferably at least about 65%, even still more preferably at least about 80–90% or greater of the molecule as determined by weight, activity or other convenient means, relative to other compounds in the composition. Most preferably, the molecule is sequencably pure.

Another preferred aspect of the present invention provides the molecule in recombinant form.

According to this aspect of the present invention, there is provided a recombinant molecule comprising a sequence of amino acids which:
  (i) is at least about 15% similar to the amino acid sequence set forth in SEQ ID NO:2; and
  (ii) is at least 5% dissimilar to the amino acid sequence set forth in SEQ ID NO:2.

A related aspect of the present invention is directed to a recombinant molecule having the following characteristics:
  (i) comprises an amino acid sequence having at least about 15% similarity but at least about 5% dissimilarity to all or part of the amino acid sequence set forth in SEQ ID NO:2;
  (ii) exhibits at least one property in common with VEGF.

A further related aspect of the present invention contemplates a recombinant molecule having the following characteristics:
  (i) comprises an amino acid sequence having at least about 15% similarity but at least about 5% dissimilarity to the amino acid sequence set forth in SEQ ID NO:2;
  (ii) exhibits at least one of the following properties:
    (a) ability to induce proliferation of vascular endothelial cells;
    (b) ability to interact with flt-1/flk-1 family of receptors;
    (c) ability to induce cell migration, cell survival and/or an increase in intracellular levels of alkaline phosphatase.

The present invention also contemplates genomic or partial genome clones encoding a proteinaceous molecule having at least about 15% amino acid similarity but at least about 5% dissimilarity to SEQ ID NO:1.

The amino acid sequence set forth in SEQ ID NO:2 corresponds to human VEGF (referred to herein as "VEGF$_{165}$"). Accordingly, the molecule of the present invention is VEGF-like or is a homologue of VEGF but comprises an amino acid sequence which is similar but non-identical to the amino sequence of VEGF. Although the present invention is exemplified using a human VEGF-like molecule, this is done with the understanding that the instant invention contemplates the homologous molecule and encoding sequence from other mammals such as livestock animals (e.g. sheep, pigs, horses and cows), companion animals (e.g. dogs and cats) and laboratory test animals (e.g. mice, rats, rabbits and guinea pigs) as well as non-mammals such as birds (e.g. poultry birds), fish and reptiles. In a most preferred embodiment, the VEGF-like molecule is of human origin and encoded by a gene located at chromosome 11q13. The present invention extends, therefore, to the genomic sequence or part thereof encoding the subject VEGF-like molecule.

Preferably, the percentage similarity is at least about 30%, more preferably at least about 40%, still more preferably at least about 50%, still even more preferably at least about 60–70%, yet even more preferably at least about 80–95% to all or part of the amino acid sequence set forth in SEQ ID NO:2.

In a particularly preferred embodiment, the VEGF-like molecule of the present invention comprises a sequence of amino acids as set forth in SEQ ID NO:4 or is a part, fragment, derivative or analogue thereof. Particularly preferred similarities include about 19–20%, and 29–30%. Reference herein to derivatives also includes splice variants. Accordingly, the present invention extends to splice variants of SOM175. Examples of splice variants contemplated by the present invention include but are not limited to variants with an amino acid sequence substantially as set forth in at least one of SEQ ID NO:6, SEQ ID NO:8 and/or SEQ ID NO:10 or mutants or derivatives or further splice variants thereof.

Another embodiment provides a recombinant molecule having the following characteristics:
  (i) an amino acid sequence substantially as set forth in SEQ ID NO:4 or having at least about 15% similarity to all or part thereof provided that said amino acid sequence is at least about 5% dissimilar to all or part of the amino acid sequence set forth in SEQ ID NO:2;
  (ii) exhibits at least one biological property in common with VEGF.

Another embodiment provides a recombinant molecule having the following characteristics:
  (i) an amino acid sequence substantially as set forth in SEQ ID NO:6 or having at least about 15% similarity to all or part thereof provided that said amino acid sequence is at least about 5% dissimilar to all or part of the amino acid sequence set forth in SEQ ID NO:2;
  (ii) exhibits at least one biological property in common with VEGF.

Another embodiment provides a recombinant molecule having the following characteristics:
  (i) an amino acid sequence substantially as set forth in SEQ ID NO:8 or having at least about 15% similarity to all or part thereof provided that said amino acid sequence is at least about 5% dissimilar to all or part of the amino acid sequence set forth in SEQ ID NO:2;
  (ii) exhibits at least one biological property in common with VEGF.

Another embodiment provides a recombinant molecule having the following characteristics:
  (i) an amino acid sequence substantially as set forth in SEQ ID NO:10 or having at least about 15% similarity to all or part thereof provided that said amino acid sequence is at least about 5% dissimilar to all or part of the amino acid sequence set forth in SEQ ID NO:2;
  (ii) exhibits at least one biological property in common with VEGF.

Such properties of VEGF include at least one of:
  (a) ability to induce proliferation of vascular endothelial cells;
  (b) an ability to interact with flt-1/flk-1 family of receptors;
  (c) an ability to induce cell migration, cell survival and/or an increase in intracellular levels of alkaline phosphatase.

In accordance with the present invention, a preferred similarity is at least about 40%, more preferably at least about 50% and even more preferably at least about 65% similarity.

Still a further aspect of the present invention contemplates a peptide fragment corresponding to a portion of the amino acid sequence set forth in SEQ ID NO:4 or a splice variant thereof such as set forth in SEQ ID NO:6, SEQ ID NO:8 or SEQ ID NO:10 or a chemical equivalent thereof. The biologically isolated or recombinant molecule of the present invention may be naturally glycosylated or may comprise an altered glycosylation pattern depending on the cells from which it is isolated or synthesised. For example, if produced by recombinant means in prokaryotic organisms, the molecule would be non-glycosylated. The molecule may be a full length, naturally occurring form or may be a truncated or otherwise derivatised form.

Yet another aspect of the present invention is directed to a nucleic acid molecule encoding the VEGF-like molecule herein described. More particularly, the present invention provides a nucleic acid molecule comprising a sequence of nucleotides substantially as set forth in SEQ ID NO:3 or having at least 15% similarity to all or part thereof or being capable of hybridising under low stringency conditions to a reverse complement of the nucleotide sequence as set forth in SEQ ID NO:3 provided that the nucleic acid sequence having at least 15% similarity but at least 30% dissimilarity to the nucleotide sequence as set forth in SEQ ID NO:3. The nucleotide sequence set forth in SEQ ID NO:3 is also referred to herein as "SOM175". Preferably, the percentage dissimilarity is about 35%, more preferably about 39% and even more preferably about 40–50% or greater.

For the purposes of defining the level of stringency, reference can conveniently be made to Sambrook et al (1989) at pages 9.47–9.51 which is herein incorporated by reference where the washing steps disclosed are considered high stringency. A low stringency is defined herein as being in 4–6×SSC/0.1–0.5% w/v SDS at 37–45° C. for 2–3 hours. Depending on the source and concentration of nucleic acid involved in the hybridisation, alternative conditions of stringency may be employed such as medium stringent conditions which are considered herein to be 1–4×SSC/0.25–0.5% w/v SDS at $\geq$45° C. for 2–3 hours or high stringent conditions considered herein to be 0.1–1×SSC/0.1% w/v SDS at 60° C. for 1–3 hours.

The present invention further contemplates a nucleic acid molecule which encodes a VEGF-like molecule as hereinbefore described having at least 15% nucleotide sequence homology to SEQ ID NO:3. Preferred levels of homology include at least about 40%, more preferably around 60–70%.

The present invention is further directed to the murine homologue of human VEGF(referral to herein as "mVRF"). The mVRF has approximately 85% identity and 92% conservation of amino acid residues over the entire coding region compared to human VEGF. The mVRF is encoded by a nucleic acid molecule comprising a nucleotide sequence substantially as set forth in FIGS. 9A–9D.

The VEGF-like molecule of the present invention will be useful in the development of a range of therapeutic and/or diagnostic applications alone or in combination with other molecules such as VEGF. The present invention extends, therefore, to pharmaceutical compositions comprising the VIEGF-like molecule or parts, fragments, derivatives, homologues or analogues thereof together with one or more pharmaceutically acceptable carriers and/or diluents. Furthermore, the present invention extends to vectors comprising the nucleic acid sequence set forth in SEQ ID NO:3 or having at least about 15%, more preferably about 40% and even more preferably around 60–70% similarity thereto but at least 30% and more preferably around 39% dissimilarity thereto and host cells comprising same. In addition, the present invention extends to ribozymes and antisense molecules based on SEQ ID NO:3 as well as neutralizing antibodies to the VEGF-like molecule. Such molecules may be useful in ameliorating the effects of, for example, over expression of VEGF-like genes leading to angiogenesis or vascularization of tumours.

Another aspect of the present invention contemplates a method of inducing astroglial proliferation in a mammal, said method comprising administering to said mammal an effective amount of a recombinant proteinaceous molecule having the characteristics:

(i) comprises an amino acid sequence having at least about 15% similarity but at least about 5% dissimilarity to the sequence set forth in SEQ ID NO:2;

(ii) exhibits at least one property in common with vascular endothelial growth factor (VEGF), said administration being for a time and under conditions sufficient to induce astroglial proliferation.

Preferably, the recombinant proteinaceous molecule comprises the amino acid sequence set forth in SEQ ID NO:3 or SEQ ID NO:6.

A further aspect of the present invention provides a method of promoting neural survival and/or proliferation in a mammal, said method comprising administering to said mammal an effective amount of a recombinant proteinaceous molecule having the characteristics:

(i) comprises an amino acid sequence having at least about 15% similarity but at least about 5% dissimilarity to the sequence set forth in SEQ ID NO:2;

(ii) exhibits at least one property in common with vascular endothelial growth factor (VEGF), said administration being for a time and under conditions sufficient to induce astroglial proliferation.

Preferably, the recombinant proteinaceous molecule comprises the amino acid sequence set forth in SEQ ID NO:3 or SEQ ID NO:6.

The present invention also contemplates antibodies to the VEGF-like molecule or nucleic acid probes to a gene encoding the VEGF-like molecule which are useful as diagnostic agents.

The present invention is further described by reference to the following non-limiting Figures and/or Examples.

In the Figures:

FIGS. 1A–1D show the nucleotide sequence (SEQ ID NO:1) and corresponding amino acid sequence (SEQ ID NO:2) of VEGF$_{165}$.

FIGS. 2A–2F show the nucleotide sequence (SEQ ID NO:3) and corresponding amino acid sequence (SEQ ID NO:4) of SOM175.

FIGS. 3A–3B show the results of BLAST search with SOM175 protein sequence.

FIGS. 4A–4D show the BESTFIT alignment of VEGF cDNA and SOM175 cDNA.

FIGS. 5A–5F show the multiple alignment of VEGF$_{165}$ with SOM175 and its splice variants at the nucleotide level.

FIGS. 6A–6C show the multiple alignment of VEGF$_{165}$ with SOM175 and its splice variants at the amino acid level.

FIG. 7 Diagrammatic representation of SOM175 and its splice variants.

FIG. 8A Diagrammatic representation of genomic structure of human SOM175 genomic showing exon/intron map.

FIG. 8B Diagrammatic representation of genomic structure of human SOM175 [SEQ ID NO.2] showing exon/intron boundries.

FIGS. 9A–9D show the nucleotide and predicted peptide sequences derived from mVRF cDNA clones. Numbering of nucleotides are given on the left, starting with the A of the initiation codon. Amino acids are numbered on the right, starting from the first residue of the predicted mature protein after the putative signal peptide has been removed. The alternatively spliced region is double underlined and the resulting peptide sequence from each mRNA is included. A potential polyadenylation signal is indicated in boldface. Start and stop codons of mVRF$_{167}$ and mVRF$_{186}$ are underlined and a polymorphic AC repeat in the 3' UTR is indicated by a stippled box. The positions of intron/exons boundaries are indicated by arrowheads.

FIGS. 10A–10B show the BESTFIT alignments of human and murine VRF protein isoforms. A: mVRF$_{167}$ and hVRF$_{167}$. B: mVRF$_{186}$ and hVRF$_{186}$ from the point where the sequences diverge form the respective 167 amino acid isoforms. Amino acid identities are marked with vertical bars and conserved amino acids with colons. An arrow marks the predicted signal peptide cleavage site of human and mouse VRF.

FIGS. 11A–11B show the BESTFIT alignment of mVRF$_{167}$ and mVEGF$_{188}$ (Brier et al., 1992) peptide sequences. An arrow marks the signal peptide cleavage site of mVEGF. Identical amino acids are indicated by vertical bars and conservative substitutions by colons. Numbering of amino acids is as described in the legend to FIG. 9.

Figure 12:
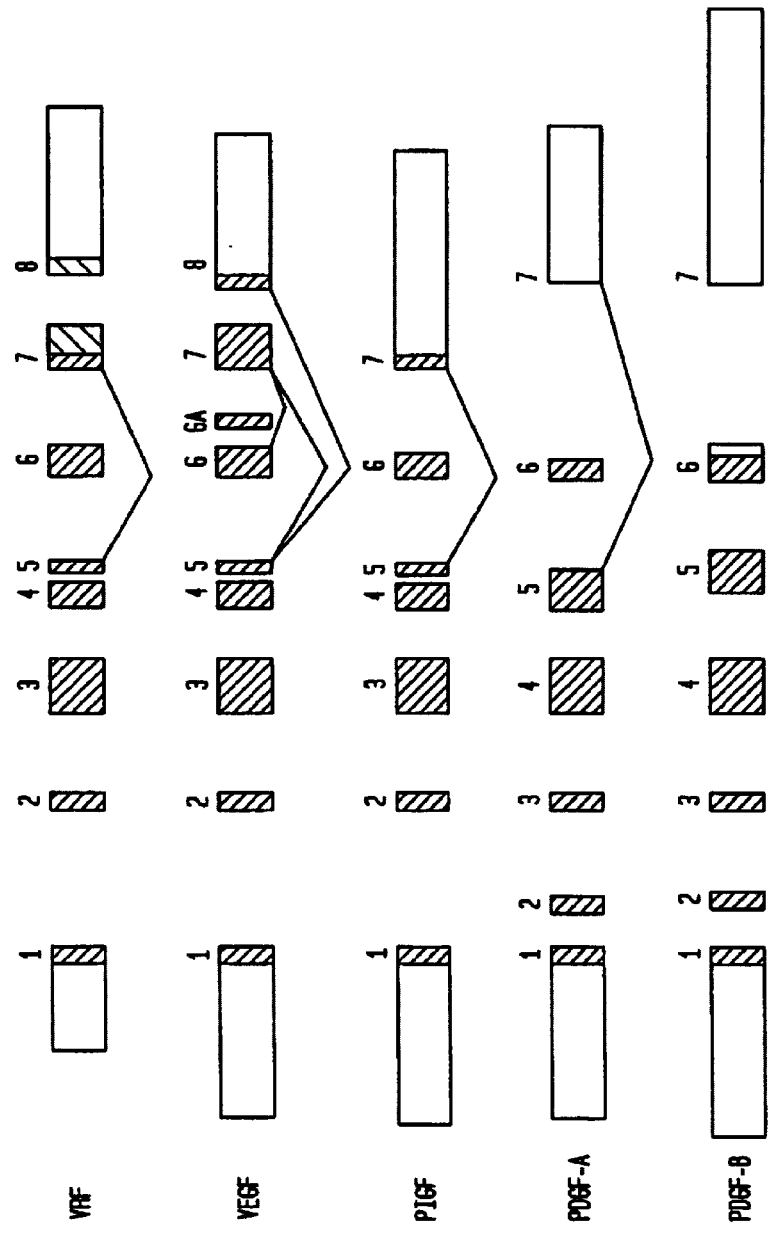

FIG. 12 Comparison of gene structure between VRF (a generic VRF gene is shown since the intron/exon organisation of the mouse and human homologues is almost identical) and other members of the human VEGF/PlGF/PDGF gene family. Exons are represented by boxes. Protein coding regions and untranslated regions are shown by filled and open sections respectively. The hatched region in VRF indicates the additional 3' UTR sequence formed by alternate splicing of the VRF$_{186}$ isoform. Potential alternate splice products of each gene are shown.

Figure 13:
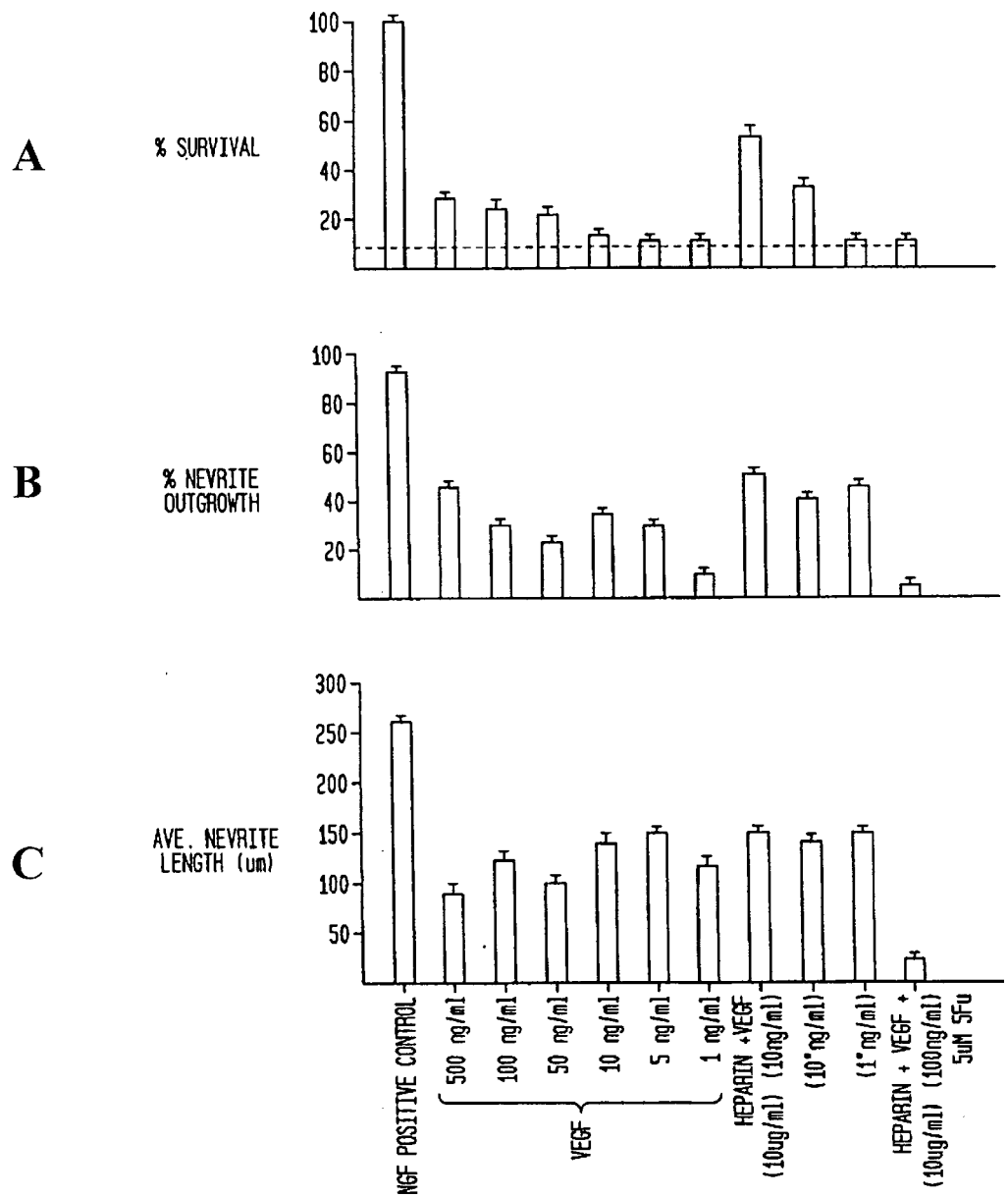

FIG. 13 Autoradiogram of a Northern blot of total RNA from various adult mouse tissues (as indicated) hybridised with an mVRF cDNA clone. A major transcript of 1.3 kb was detected in all samples.

FIGS. 14A–14E show film autoradiographs (A–C) and dark-field micrographs (D–E) illustrating the expression pattern of mVRF and mRNA in the mouse. In the E14 mouse embryo (A) positive signals are present over the developing heart (Ha) and cerebral cortex (Cx). A low background signal is also present over other tissues in the section. In the E17 embryo (B) and the heart (Ha) is clearly visible due to a strong hybridisation signal. An equally strong signal is present over brown adipose tissue (Fa) in the back and around the thoracic cage. A moderate hybridisation signal is present over the spinal cord (SC) and the tongue (T). The background signal is reduced compared with the E14 embryo. In the young adult mouse (C–D), positive signals are present over the heart (Ha) and adipose tissue (Fa) around the thoracic cage, while, for example, the lungs (Lu) are unlabeled). The hybridisation signal over the heart is evenly distributed over the entire left ventricle, including papillary muscles (D). In the E17 heart hybridised with an excess of cold probe, no positive signal is present (E). Scale bars=0.5 mm (A), 1.2 mm (B), 1 mm (C), 0.3 mm (D), 0.1 mm (E).

FIGS. 15A–15D show dark—(A and C) and bright-field (B and D) micrographs showing mVRF mRNA expression in mouse adipose tissue (A–B) and spinal cord (C–D). A strong hybridisation signal is present over fat (A), as shown by the strong labeling in Sudan black stained sections (B). A weak signal is present also in skeletal muscle (M in A–B). In the adult spinal cord (C) the mVRF probes gave a neuronal staining pattern over the gray matter. Toloudine counterstaining showing that motoneurons in the ventral horn (D), interneurons in the deep part of the dorsal horn and around the central canal (not shown) where largely positive for mVRF mRNA. Scale bars=0.1 mm (A), 0.1 mm (B), 0.25 mm (C), 0.015 mm (D).

FIGS. 13A–13C show the effect of VEGF on embryonic day (E8) chick sensory neurons as determined by % survival (FIG. 13A), % neurite outgrowth (FIG. 13B) and average neurite length (µm) (FIG. 13C).

FIGS. 14A–14C show the effects of VEGF and SOM175 on chick glia. Tested were CNS glial (FIG. 14A), peripheral glia (FIG. 14B) and CNS oligodendrocytes (FIG. 14C)

FIG. 15 Effect of various SOM175 proteins on mouse astroglial cells. [$^3$H (cpm)

1. FGF-2 (10 ng/ml) positive control
2. SOMΔX6* 1 ng/ml
3. SOMΔX6 10 ng/ml
4. SOMΔX6 100 ng/ml
5. SOMΔX6 1000 ng/ml
6. SOMΔX6 1000 ng/ml, no heparin
7. SOMX6** 1 ng/ml
8. SOMX6 10 ng/ml
9. SOMX6 100 ng/ml
10. SOMX6 1000 ng/ml
11. SOMX6 1000 ng/ml, no heparin

*This refers to SOM175 absent exon 6;
**This refers to SOM175.

FIG. 16 Effect of various SOM175 proteins on mouse oligodenroglial cells. ■$^3$H (cpm)

1. FGF-2 (10 ng/ml) positive control
2. SOMΔX6* 1 ng/ml
3. SOMΔX6 10 ng/ml
4. SOMΔX6 100 ng/ml
5. SOMΔX6 1000 ng/ml
6. SOMΔX6 1000 ng/ml, no heparin
7. SOMX6** 1 ng/ml
8. SOMX6 10 ng/ml
9. SOMX6 100 ng/ml
10. SOMX6 1000 ng/ml
11. SOMX6 1000 ng/ml, no heparin This refers to SOM175 absent exon 6;
This refers to SOM175.

FIG. 17 Effect of various SOM175 proteins on mouse forebrain neurons. ■% survival 1. FGF-2 (10 ng/ml) positive control
2. SOMΔX6* 1 ng/ml
3. SOMΔX6 10 ng/ml
4. SOMΔX6 100 ng/ml
5. SOMΔX6 1000 ng/ml
6. SOMΔX6 1000 ng/ml, no heparin
7. SOMX6** 1 ng/ml
8. SOMX6 10 ng/ml
9. SOMX6 100 ng/ml
10. SOMX6 1000 ng/ml
11. SOMX6 1000 ng/ml, no heparin This refers to SOM175 absent exon 6;
This refers to SOM175.

TABLE 1

SUMMARY OF SEQUENCE IDENTITY NUMBERS

| | |
|---|---|
| SEQ ID NO:1 | Nucleotide sequence of VEGF$_{165}$ |
| SEQ ID NO:2 | Amino acid sequence of VEGF$_{165}$ |
| SEQ ID NO:3 | Nucleotide sequence of SOM175 (VEGF-like molecules) |
| SEQ ID NO:4 | Amino acid sequence of SOM175 |
| SEQ ID NO:5 | Nucleotide sequence of SOM175 absent exon 6 |
| SEQ ID NO:6 | Amino acid sequence of SOM175 absent exon 6 |
| SEQ ID NO:7 | Nucleotide sequence of SOM175 absent exon 6 and exon 7 |
| SEQ ID NO:8 | Amino acid sequence of SOM175 absent exon 6 and exon 7 |
| SEQ ID NO:9 | Nucleotide sequence of SOM175 absent exon 4 |
| SEQ ID NO:10 | Amino acid sequence of SOM175 absent exon 4 |
| SEQ ID NO:11 | Oligonucleotide |
| SEQ ID NO:12 | Oligonucleotide |
| SEQ ID NO:13 | Oligonucleotide |
| SEQ ID NO:14 | Oligonucleotide |

EXAMPLE 1

Human cDNA Clones

The original SOM175 cDNA was isolated by screening a human foetal brain library (λzapII, Stratagene) with the cosmid D11S750 (Larsson et al, 1992). The plasmid was excised "in vivo" and a single 1.1 kb cDNA was obtained. Three independent SOM175 cDNAs clones were also isolated from a human foetal spleen library (Strategane, Unizap) using the above-mentioned SOM175 insert as a probe. Three clones were obtained: SOM175-4A, -5A and -6A. SOM175-5A is an alternately spliced clone with exon 4 being absent (SOMl 75-e4). These library screens were performed using hybridisation conditions recommended by the manufacturer of the library (Stratagene) and random primed insert of SOM175.

Two partial human SOM175 cDNAs have also isolated from a λGT11 human melanoma cell line A2058 library (Clontech) cDNA library screens were performed using hybridisation conditions described by Church and Gilbert, 1984). In each case, the probe was generated by random priming of a PCR product derived from SOM175 (18f-700r).

Mouse cDNA Clones

Human SOM175 was also used to screen a mouse neonatal whole brain cDNA library (Unizap, Stratagene). Four non-chimeric clones were isolated: M175-A, B, C, D. All clones were partial cDNAs and M175-C contained several introns. Three of these cDNAs lacked the exon 6.

Another clone referred to as M1 was completely sequenced and was found to contain the full open reading frame plus part of the 5' utr and total 3' utr.

EXAMPLE 2

DNA Sequence Analysis

The entire sequence of the cDNA clone (SOM175) was compiled and is shown in FIGS. 2A–2F with its corresponding amino acid sequence. This sequence was screened for open reading frames using the MAP program (GCG, University of Wisconsin). A single open reading frame of 672 bp was observed (see FIGS. 2A–2F). There appears to be little 5' untranslated sequences (2 bp). The 3' untranslated region appears to be complete as it includes a poly-adenylation signal poly-A tail.

Database homology searches were performed using the BLAST algorithm (run at NCBI, USA). This analysis revealed homology to several mammalian forms of VEGF (see FIGS. 3A–3B). The amount of homology between SOM175 and human VEGF$_{165}$ was determined using the BESTFIT program (GCG, University of Wisconsin; see FIGS. 4A–4D and 5A–5F). Nucleotide homology was estimated at 69.7% and protein homology was estimated as at least 33.3% identity and 52.5% conservation using BESTFIT analysis. BLAST analysis on nucleotide sequences revealed the almost complete match to a human expressed sequence tag EST06302 (Adams et al., 1993).

Figure 6B:
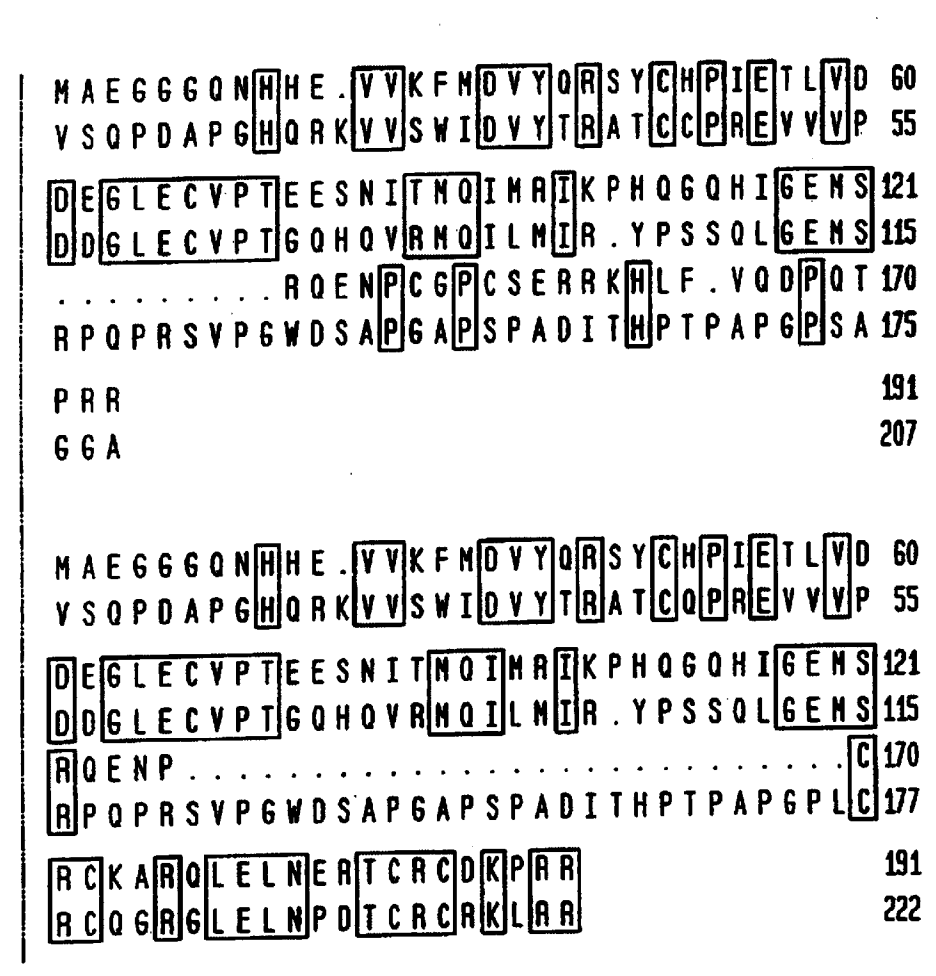

These data indicate that SOM175 encodes a growth factor that has structural similarities to VEGF. Both genes show start and stop codons in similar positions and share discrete blocks of homology. All 8 cysteines as well as a number of other VEGF residues believed to be involved in dimerisation are conserved. These residues are Cysteine-47, Proline-70, Cysteine-72, Valine-74, Arginine-77, Cysteine-78, Glycine-80, Cysteine-81, Cysteine-82, Cysteine-89, Proline-91, Cysteine-122 and Cysteine-124 and are shown in FIGS. 6A–6C. Given the structural conservation between VEGF and the SOM175 gene product it is also possible that they share functional similarities. It is proposed that SOM175 encodes a VEGF-like molecule that shares some properties with VEGF but has unique properties of its own. The nucleotide sequence and corresponding amino acid sequence of VEGF$_{165}$ is shown in FIGS. 1A–1D.

EXAMPLE 3

The percentage similarity and divergence between VEGF$_{165}$ family and SOM175 family (protein) were analysed using the Clustal method, MegAlign Software, DNASTAR, Wisconsin. The results are shown in Tables 2.1 and 2.2. The alternatively spliced forms of SOM175 are abreviated to SOM715-e6 where all of exon 6 is deleted; SOM715-e6 and 7 where all of exons 6 and 7 are deleted; and SOM175-e4 where all of exon 4 is deleted. The spliced form of SOM175 are shown in FIG. 7. Genomic maps of SOM175 showing intron/exon boundaries are shown in FIGS. 8A and 8B.

TABLE 2.1

|  | VEGF$_{165}$ | SOM175 | SOM175-e6 | SOM175-e6&7 | SOM175-e4 |
|---|---|---|---|---|---|
| A Percent nucleotide similarity between splice variants of SOM175 and human VEGF$_{165}$ | | | | | |
| VEGF$_{165}$ | *** | 34.9 | 39.7 | 41.4 | 37.0 |
| SOM175 |  | *** | 98.9 | 95.1 | 99.2 |
| SOM175-e6 |  |  | *** | 98.8 | 84.0 |
| SOM175-e6&7 |  |  |  | *** | 80.3 |
| SOM175-e4 |  |  |  |  | *** |
| B Percent nucleotide divergence between splice variants of SOM175 and human VEGF$_{165}$ | | | | | |
| VEGF$_{165}$ | *** | 41.7 | 41.6 | 41.7 | 41.8 |
| SOM175 |  | *** | 0.2 | 0.2 | 0.0 |
| SOM175-e6 |  |  | *** | 0.0 | 0.2 |
| SOM175-e6&7 |  |  |  | *** | 0.3 |
| SOM175-e4 |  |  |  |  | *** |

TABLE 2.2

|  | VEGF$_{165}$ | SOM175 | SOM175-e6 | SOM175-e6&7 | SOM175-e4 |
|---|---|---|---|---|---|
| A Percent amino acid identity between splice variants of SOM175 and human VEGF$_{165}$ | | | | | |
| VEGF$_{165}$ | *** | 31.4 | 42.3 | 33.5 | 40.6 |
| SOM175 |  | *** | 74.7 | 73.7 | 99.1 |
| SOM175-e6 |  |  | *** | 76.8 | 99.1 |
| SOM175-e6&7 |  |  |  | *** | 99.1 |
| SOM175-e4 |  |  |  |  | *** |
| B Percent amino acid divergence between splice variants of SOM175 and human VEGF$_{165}$ | | | | | |
| VEGF$_{165}$ | *** | 65.7 | 55.4 | 54.6 | 57.4 |
| SOM175 |  | *** | 19.9 | 4.2 | 0.0 |
| SOM175-e6 |  |  | *** | 0.0 | 0.0 |
| SOM175-e6&7 |  |  |  | *** | 0.0 |
| SOM175-e4 |  |  |  |  | *** |

EXAMPLE 4

Bioassays to Determine the Function of SOM175

Assays are conducted to evaluate whether SOM175 has similar activities to VEGF on endothelial cell function, angiogenesis and wound healing. Other assays are performed based on the results of receptor binding distribution studies.

Assays of Endothelial Cell Function

Endothelial cell proliferation. Endothelial cell growth assays as described in Ferrara & Henzel (1989) and in Gospodarowicz et al (1989).

Vascular permeability assay. This assay, which utilises the Miles test in guinea pigs, will be performed as described in Miles & Miles (1952).

Cell adhesion assay. The influence of SOM175 on adhesion of polymorphs to endothelial cells is analysed.

Chemotaxis. This is performed using the standard Boyden chamber chemotaxis assay.

Plasminogen activator assay. Endothelial cells are tested for plasminogen activator and plasminogen activator inhibitor production upon addition of SOM175 (Pepper et al (1991)).

Endothelial cell migration assay. The ability of SOM175 to stimulate endothelial cells to migrate and form tubes is assayed as described in Montesano et al (1986).

Angiogenesis Assay

SOM175 induction of an angiogenic response in chick chorioallantoic membrane is evaluated as described in Leung et al (1989).

Possible neurotrophic actions of SOM175 are assessed using the following assays:

Neurite Outgrowth Assay and Gene Induction (PC12 Cells)

PC12 cells (a phaeochromocytoma cell line) respond to NGF and other neurotrophic factors by developing the characteristics of sympathetic neurons, including the induction of early and late genes and the extension of neurites. These cells are exposed to SOM175 and their response monitored (Drinkwater et al (1991); and Drinkwater et al (1993)).

Cultured Neurons from the Peripheral Nervous System (PNS)

Primary cultures of the following PNS neurons are exposed to SOM175 and monitored for any response:
   sensory neurons from neural crest and dorsal root ganglia
   sympathetic neurons from sympathetic chain ganglia
   placode derived sensory neurons from nodose ganglia
   motoneurons from spinal cord The assays are described in Suter et al (1992) and in Marinou et al (1992).

Where an in vitro response is observed, in vivo assays for properties such as uptake and retrograde transport are performed as described in Hendry et al (1992).

Nerve Regeneration (PNS)

Where neurotrophic effects of SOM175 are observed, its possible role in the regeneration of axotomised sensory neurons, sympathetic neurons and motoneurons is analysed by the methods of Otto et al (1989); Yip et al (1984) and Hendry et al (1976).

Actions of SOM175 on CNS Neurons

The ability of SOM175 to promote survival of central nervous system neurons is analysed as described in Hagg et al (1992); Williams et al (1986); Hefti (1986) and Kromer (1987).

Wound Healing

The ability of SOM1 75 to support wound healing are tested in the most clinically relevant model available, as described in Schilling et al (1959) and utilised by Hunt et al (1967).

The Haemopoietic System

A variety of in vitro and in vivo assays on specific cell populations of the haemopoietic system are available and are outlined below:

Stem Cells
   Murine

A variety of novel in vitro murine stem cell assays have been developed using FACS-purified cells:

(a) Repopulating Stem Cells

These are cells capable of repopulating the bone marrow of lethally irradiated mice, and have the Lin$^-$, Rh$^{hi}$, Ly-6A/E$^+$, c-kit$^+$ phenotype. The test substance is tested on these cells either alone. or by co-incubation with multiple factors, followed by measurement of cellular proliferation by $^3$H thymidine incorporation.

(b) Late Stage Stem Cells

These are cells that have comparatively little bone marrow repopulating ability but can generate D13 CFU-S. These cells have the Lin$^-$, Rh$^{hi}$, Ly-6A/E$^+$, c-kit$^+$ phenotype. The test substance is incubated with these cells for a period of time, injected into lethally irradiated recipients, and the number of D13 spleen colonies enumerated.

(c) Progenitor-Enriched Cells

These are cells that respond in vitro to single growth factors, and have the Lin$^-$, R$^{hi}$, Ly-6A/E$^+$, c-kit$^-$ phenotype. This assay will show if SOM175 can act directly on haemopoietic progenitor cells. The test substance is incubated with these cells in agar cultures, and the number of colonies enumerated after 7–14 days.

Atherosclerosis

Smooth muscle cells play a crucial role in the development or initiation of atherosclerosis, requiring a change in their phenotype from a contractile to a synthetic state. Macrophages. endothelial cells, T lymphocytes and platelets all play a role in the development of atherosclerotic plaques by influencing the growth and phenotypic modulations of smooth muscle cell. An in vitro assay that measures the proliferative rate and phenotypic modulations of smooth muscle cells in a multicellular environment is used to assess the effect of SOM175 on smooth muscle cells. The system uses a modified Rose chamber in which different cell types are seeded onto opposite coverslips.

Effects of SOM175 on Bone

The ability of SOM175 to regulate proliferation of osteoblasts is assayed as described in Lowe et al (1991). Any effects on bone resorption are assayed as described in Lowe et al (1991). Effects on osteoblast migration and changes in intracellular molecules (e.g. cAMP accumulation, alkaline phosphatase levels) are analysed as described in Midy et al (1994).

Effects on Skeletal Muscle Cells

Effects of SOM175 on proliferation of myoblasts and development of myotubes can be determined as described by Ewton et al (1980) and by Gospodarowicz et al (1976).

EXAMPLE 5

Cloning Murine VEGF DNA

Isolation of cDNAs

Murine VRF (mVRF) clones were selected from a lambda Zap new born whole brain cDNA library (Stratagene). Primary phage from high density filters (5×10$^4$ pfu/plate) were identified by hybridisation with a 682 bp $^{32}$P-labelled probe generated by PCR from an hVRF cDNA (pSOM175) as described above. Hybridisation and stringent washes of nylon membranes (Hybond-N) were carried out at 65° C. under conditions described by Church and Gilbert (1984). Positive plaques were picked, purified and excised in vivo to produce bacterial colonies containing cDNA clones in pBluescript SK–.

Isolation of Genomic Clones

Genomic clones were isolated from a mouse strain SV/129 library cloned in the lambda Fix II vector (Stratagene). High density filters (5×10$^4$ pfu/filter) were screened with a 563 bp $^{32}$P-labelled probe generated by PCR amplification of the nucleotide 233–798 region of the mVRF cDNA (see FIG. 9). Positive clones were plugged and re-screened with filters containing 400–800 pfu. Large scale phage preparations were prepared using the QIAGEN lambda kit or by ZnCl$_2$ purification (Santos, 1991).

Nucleotide Sequencing and Analysis cDNAs were sequenced on both strands using a variety of vector-based and internal primers with Applied Biosystems Incorporated (ABI) dye terminator sequencing kits according to the manufacturer's specifications. Sequences were analysed on an ABI Model 373A automated DNA sequencer. Peptide homology alignments were performed using the program BESTFIT (GCG, Wisconsin).

Identification of Intron/exon Boundaries

Identification of exon boundaries and flanking regions was carried out using PCR with mouse genomic DNA or mVRF genomic lambda clones as templates. The primers used in PCR to identify introns were derived from the hVRF sequence and to allow for potential human-mouse sequence mismatches annealing temperatures 5° C. below the estimated T$_m$ were used. All PCR products were sized by agarose gel electrophoresis and gel purified using QIAquick spin columns (Qiagen) and the intron/exon boundaries were sequenced directly from. these products. In addition, some splice junctions were sequenced from subcloned genomic fragments of MVRF. Intron/exon boundaries were identified by comparing cDNA and genomic DNA sequences.

Northern Analysis

Total cellular RNA was prepared from a panel of fresh normal adult mouse tisues (brain, kidney, liver, muscle) using the method of Chomczynski and Sacchi (1987). 20 µg of total RNA were electrophoresed, transferred to a nylon membrane (Hybond N, Amersham) and hybridised under standard conditions (Church & Gilbert, 1984). Filters were washed at 65° C. in 0.1×SSC (20×SSC is 3M NaCl/0.3M trisodium citrate), 0.1% SDS and exposed to X-ray film with intensifying screens at −70° C. for 1–3 days.

Characterisation of mVRF cDNAs

Murine VRF homologues were isolated by screening a murine cDNA library with an hVRF cDNA clone. Five clones of sizes varying from 0.8–1.5 kb were recovered and sequenced. The cDNA sequences were compiled to give a full length 1041 bp cDNA sequence covering the entire open reading frame (621 bp or 564 bp depending on the splice form, see below) and 3' UTR (379 bp), as well as 163 bp of the 5' UTR (FIGS. 9A–9D).

The predicted initiation codon matched the position of the start codon in hVRF. One other out of frame ATG was located at position −47 and two termination codons were observed upstream (positions −9 and −33, respectively) and in-frame with the putative The predicted N-terminal signal peptide of hVRF appears to be present in mVRF with 81% identity (17/21 amino acids). Peptide cleavage with mVRF is expected to occur after reside 21 (FIGS. 10A–10B). These data suggest that mature mVRF is secreted and could therefore conceivably function as a growth factor.

As with hVRF, two open reading frames (ORFs) were detected in cDNAs isolated by library screening. Four of five clones were found to be alternatively spliced and lacked a 101 bp fragment homologous to exon 6 of hVRF. The predicted peptide sequences of the two isoforms of mVRF were determined and aligned with the corresponding human isoforms (FIGS. 10A–10A.

The message encoding $mVRF_{186}$ contains a 621 bp ORF with coding sequences terminating at position +622, towards the end of exon 7 (FIGS. 9A–9D). The smaller message encoding $mVRF_{167}$ actually terminates downstream of the +622 TAG site due to a frame shift resulting from splicing out of the 101 bp exon 6 and the introduction of a stop codon (TGA) at position +666, near the beginning of exon 8 (FIGS. 9A–9D).

The $mVRF_{186}$ protein has strong homology to the amino and central portions of VEGF while the carboxyl end is completely divergent and is alanine rich. $mVRF_{167}$ possesses these similarities and also maintains homology to mVEGF right through to the C-terminus (FIGS. 11A–11B). The overall homology of $mVRF_{167}$ to $hVRF_{167}$ was 85% identity and 92% similarity, respectively (FIGS. 10A–10B). Likewise, homology between $mVRF_{167}$ and mVEGF (Breier, et al. 1992) was 49% identity and 71% conservative amino acid substitution, respective (FIGS. 11A–11B).

A canonical vertebrate polyadenylation signal (AATAAA) (Birnstiel, et al., 1986) was not present in the mVRF cDNA, however, the closely matching sequence GATAAA is present at similar positions in both mouse and human VRF cDNAs (FIGS. 9A–9D). In contrast to hVRF, mVRF was found to contain an AC dinucleotide repeat at the extreme 3' end of the 3' UTR (nucleotide positions 998 to 1011, FIGS. 9A–9D). Polymorphism of this repeat region was observed between some of the mVRF cDNAs, with the number of dinucleotides varying from 7 to 11.

Genomic Characterisation of mVRF

Intron/exon boundaries (Table 3). were mapped using primers which flanked sequences homologous to the corresponding hVRF boundaries. Introns I, III, IV and VI of mVRF (Table 3, FIG. 12) were smaller than the hVRF intervening sequences. The complete genomic sequence was compiled from the 5' UTR of mVRF through to intron VI, the largest intervening region (2.2 kb), by sequencing amplified introns and cloned genomic portions of mVRF. There was only one major difference in genomic structure between mVRF and hVRF and that was the exon 7/intron VI boundary of mVRF was located 10 bp further downstream in relation to the cDNA sequence, hence exon 7 in mVRF is 10 bp longer than the corresponding exon in hVRF.

Exons 6 and 7 are contiguous in mVRF, as has been found to occur in the human homologue. The strong sequence homology between exon 6 of mVRF and hVRF (FIGS. 10A–10B) suggests that this sequence is not a retained intronic sequence but rather encodes a functional part of the $VRF_{186}$ isoform.

General intron/exon structure is conserved between the various members of the VEGF gene family (VEGF, PIGF, hVRF) and therefore it is not surprising that the overall genomic organization of the mVRF gene is very similar to these genes (FIG. 12).

Previous comparative mapping studies have shown that the region surrounding the human multiple endocrine neoplasia type I disease locus on chromosome 11q13 is syntenic with the proximal segment of mouse chromosome 19 (Rochelle et al, 1992). Since the inventors have mapped the hVRF gene to within 1 kb of the human MEN1 locus (see above) it is most likely that the murine VRF gene maps near the centromere of chromosome 19.

Expression Studies of mVRF

Northern analysis of RNA from adult mouse tissues (muscle, heart, lung and liver) showed that expression appears to be ubiguitous and occurs primarily as a major band of approximately 1.3 kb in size. This is somewhat different to the pattern observed for hVRF in which two major bands of 2.0 and 5.5 kb have been identified in all tissues examined. The 1.3 kb murine message presumably corresponds to the shorter of the human transcripts and the size variation thereof is most likely due to a different in the length of the respective 5' UTRs.

EXAMPLE 6

Expression of Murine VEGF in PRE- and Post-natal Mouse

Animals

Timed pregnant (n=4) and young adult (n=2) mice (C57 inbred strain, ALAB, Sweden) were sacrificed with carbon dioxide, and the relevant tissues were taken out and frozen on a chuck. Tissues were kept at −70° C. until further use. Two gestational ages was used in this study; embryonic day 8 (E8), 14 and E17.

In situ Hybridisation Histochemistry

In situ hybridisation was performed as previously described (Dagerlind et al, 1992). Briefly, transverse sections (14 µm) were cut in a cryostat (Microm, Germany), thawed onto Probe-On slides (Fisher Scientific, USA) and stored in black sealed boxes at −70° C. until used. The sequences of the synthetic 42-mer oligonucleotides complementary to mRNA encoding mVRF were ACCACCAC-CTCCCTGGGCTGGCATGTGGCACGTGCATAAACG [SEQ ID NO:11] (complementary to nt 120–161) and AGT-TGTTTGACCACATTGCCCATGAGTTC-CATGCTCAGAGGC [SEQ ID NO:12] (complementary to nt 162–203). To detect the two alternative splice forms oligonucleotide GATCCTGGGGCTGGAGTGGGATG-GATGATGTCAGCTGG [SEQ ID NO:13] (complementary to nt xxx-xxx) and GCGGGCAGAGGATCCTGGGGCT- GTCTGGCCTCACAGCACT [SEQ ID NO:14] were used. The probes were labeled at the 3'-end with deoxyadenosine-alpha[thio]triphosphate [$^{35}$] (NEN, USA) using terminal deoxynucleotidyl transferase (IBI, USA) to a specific activity of 7–10×10$^8$ cpm/ g and hybridised to the sections without pretreatment for 16–18 h at 42° C. The hybridisation mixture contained: 50% v/v formamide, 4×SSC (1×SSC= 0.15M NaCl and 0.015M sodium-citrate), 1×Denhardt's solution (0.02% each of polyvinyl-pyrrolidone, BSA and Ficoll) 1% v/v sarcosyl (N-lauroylsarcosine; Sigma), 0.02M phosphate buffer (pH 7.0), 10% w/v dextran sulfate (Pharmacia, Sweden), 250 µg/ml yeast tRNA (Sigma), 500 µg/ml sheared and heat denatured salmon sperm DNA (Sigma) and 200 mM dithiothreitol (DTT; LKB, Sweden). In control sections, the specificity of both probes was checked by adding a 20-fold excess of unlabeled probe to the hybridisation mixture. In addition, adjacent sections were hybridised with a probe unrelated to this study which gave a different expression pattern. Following hybridisation the sections were washed several times in 1×SSC at 55° C., dehydrated in ethanol and dipped in NTB2 nuclear track emulsion (Kodak, USA). After 3–5 weeks the sections were development in D-19 developer (Kodak, USA) and cover-slipped. In some cases, sections were opposed to an autoradiographic film (Beta-max autoradiography film Amersham Ltd, UK) prior to emulsion-dipping.

The four different probes gave identical hybridisation patterns in all tissues examined. Mouse VRF expression was detecting already in the E8 embryo, in which positive signal was recorded over structures most likely corresponding to the neuronal tube. In sagittal sections of E14 mouse embryo the strongest hybridisation signal was present over heart and in the nervous system, especially cerebral cortex. A low level of expression was present in all other tissues. At a later gestational age, E17, a high mVRF mRNA signal was confined to he heart and brown fat tissue in the back and around the neck. Clearly positive hybridisation signals were present in the gray of the spinal cord and in the tongue. Expression in the cerebral cortex was clearly reduced compared to day 14. The weak background expression seen in the E14 embryo in for example muscle, had decreased at this gestational age. A strong mVRF mRNA hybridisation signal was present solely over the heart and in the brown fat in the young adult mice. The signal over the heart was evenly distributed ove the entire ventricular wall, including the papillary muscles. In sections of heart tissue hybridised with an excess of cold probe, no specific labeling over background signal was recorded.

Apart from the heart, mVRF mRNA signal was present over certain tissues on the outside of the thoracic cage that morphologically resembled brown fat. This was verified with sudan black counterstaining, which showed a strong staining in the same areas. In transverse sections of adult mouse spinal cord, the mVRF probes gave a neuronal staining pattern over the gray matter. Counterstaining with toluidine showed that motoneurons in the ventral horn, interneurons in the deep part of the dorsal horn and around the central canal where to a large extent positive for mVRF mRNA.

EXAMPLE 7

Effects of VEGF and SOM175 Proteins on Chick Sensory Neurons

The effects of VEGF and SOM175 proteins on embryonic day 8 chick sensory neurons were determined using the method of Nurcombe et al (1992). The neuronal assay was read at 48 hours using 2000 cells per assay well. The results were obtained using $^3$H-thymidine counts. The percentage survival of neurons, neurite outgrowth and average neurite length in µm were determined using NGF as positive control and various concentrations of VEGF, VEGF in the presence of heparin and VEGF in the presence of heparin and 5 µM, 5'-flurouracil (5FU). 5FU kills glial cells.

The results are shown in FIGS. 13A–13C. The results show that VEGF is effective in promoting neuronal survival but that this requires the presence of glial cells. FIGS. 14A–14C show the results of the effect of VEGF and SOM175 on three types of chick glia. The glia tested were CNS glia (FIG. 14A), peripheral glia (FIG. 14B) and CNS oligodendrocytes (FIG. 14C). Heparin was used at 10 µg/ml in all cultures and the assay was read at 24 hours. Results were measured in $^3$H-thymidine counts using 2000 cells per well.

The results show that for chick central and peripheral neurons, astroglia were markedly stimulated to proliferate by SOM175 in the presence of heparin but that chick oligodendrocytes showed negligible increase in the rate of division.

EXAMPLE 8

Effects of SOM175 Proteins on Mouse Primary and Central Neurons

The results in Example 7 show that VEGF isoform had an effect on chick primary and central neurons through the agency of the astroglial cells. Similar experiments were repeated in mouse cells.

Culture Conditions

Neuronal and gligal cells for all in vitro experiments were prepared and cultured according o the techniques described in "Methods in Neurosciences (Vol. 2): Cell Culture" Ed. P. M. Conn, Academic Press, San Diego, 1990, pp33–46 for astroglial cells, pp56–74 for oligodendroglial cells, and pp87–102 for central neurons.

Cells were plated onto 24-well culture clusters (Nunc) coated with poly-L-ornithine (0.1 mg/ml, 1 h) at a density of 2,000 cells/well. After 48 hours in culture, neurons were counted in the wells under inverted phase light using well established techniques (Maruta et al. 1993) and glial cells assessed with [$^3$H]thymidine uptake to monitor cell division rates as below. Heparin (10 µg/ml, low molecular weight fraction, Sigma Chemical Corp.) was present at. all times in the culture media except where noted. The neuronal cultures were supplemented with 5 mM 5-fluoro-2-deoxyuridine (Sigma) to suppress background glial growth.

$^3$H-Thymidine Incorporation Assay for Glial Cell Proliferation

The cells were pulsed for 14 h with $^3$H-thymidine (specific activity 103 µCi/ug) fraom a stock concentration of 0.1 mCi/ml in standard medium, giving a final incubating volume of 20 µl/well. The contents of the wells were harvested and absorbed onto nitrocellulose paper (Titertek, Flow). Remaining adherent cells were removed by incubation with trypsin/versene (CSL Limited, Victoria, Australia) for 5 min. This procedure was carried out twice. The nitrocellulose discs were washed in a standard Titertek harvester (Flow) using first distilled water, and then methanol. The nitrocellulose discs were dried, scintillation fluid (containing 5% v/v Triton-X) added and the discs counted on a scintillation counter.

Greatest activity was seen with preparations of SOM175 absent exon 6 (SOMΔX6) on mouse astroglial cell cultures, where there was a significant stimulus to their proliferation when delivered in conjunction with heparin (FIGS. 13A–13C). Little stimulus was given to the proliferation of oligodendroglial cells FIGS. (14A–14C), and very little discernable potentiation of the survival response of isolated forebrain neurons (FIG. 15). The standard deviation on all three graphs for each point was less than 8%.

The viability of neurons can be maintained by promoting glial cell proliferation. Furthermore, SOMΔX6 is a good inducer of astroglial proliferation and may be expressed in conjunction with the formation of astroglial endfeet on central nervous system endothelial cells.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 3

Splice junctions of the murine VRF gene

| 5' UTR* ... | Exon 1 | >223 bp | CCCAGgtacgtgcgt | Intron I | 495 bp |
|---|---|---|---|---|---|
| ttccccacagGCCCC | Exon 2 | 43 bp | GAAAGgtaataatag | Intron II | 288 bp |
| ctgcccacagTGGTG | Exon 3 | 197 bp | TGCAGgtaccagggc | Intron III | 196 bp |
| ctgagcacagATCCT | Exon 4 | 74 bp | TGCAGgtgccagccc | Intron IV | 182 bp |
| ctcttttcagACCTA | Exon 5 | 36 bp | GACAGattcttggtg | Intron V | 191 bp |
| ctcctcctagGGTTG | Exon 6 | 101 bp | | (no intron) | |
| CCCACTCCAGCCCCA | Exon 7 | 135 bp | TGTAGgtaaggagtc | Intron VI | ~2200 bp |
| cactccccagGTGCC | Exon 8 | 394 bp | AGAGATGGAGACACT | | |

Uppercase and lowercase letters denote exonic and intronic sequences respectively.
*Indicates that the 5' end of exon 1 has not yet been determined.

Bibliography

Adams M D, Soares M B, Kerlavage A R, Fields C, Venter J C, (1993) *Nature Genet*, 4, 373–380.
Birnstiel M L, Busslinger M and Strub K (1985) *Cell* 41, 349–359.
Breier G, Albrecht U, Sterrer S and Risau W (1992) *Development* 114, 521–532.
Chomczynski P and Sacchi N (1987) *Analyt. Biochem.* 162, 156–159.
Church G and Gilbert W (1984) *Proc. Natl. Acad. Sci. USA* 18, 1991–1995.
Dagerlind A, Friberg K, Bean A J and Hokfelt T (1992) *Histochemistry* 98, 39–49.
Dissen G A, Lara H E, Fabrenbach W H, Costa M E, Ojeda S R, (1994) *Endocrinology* 134, 1146–1154.
Drinkwater C C, Barker P A, Suter U and Shooter E M (1993) *J. Biol. Chem.*, 268, 23202–23207.
Drinkwater C C, Suter U, Angst C and Shooter E M (1991) *Proc. Roy. Soc. Lond. (Series B)*, 246, 307–313.
Ewton D Z & Florini J R (1980) *Endocrinology*, 106: 577–583.
Ferrara N & Henzel W J (1989) *Biochem. Biophys. Res. Commun.* 161, 851–858.
Folkman J & Shing Y (1992) *J. Biol. Chem.* 267, 10931–10934.
Gospodarowicz D, Abraham J A & Schilling J (1989) *Proc. Natl. Acad. Sci USA* 86, 7311–7315.
Gospodarowicz D, Weseman J, Morgan J S & Lindstrom J (1976) *J. Cell Biol.*, 70: 395–405.
Hagg T, Quon D, Higaki J & Varon S (1992) *Neuron*, 8, 145–158.
Hefti S (1986) *J. Neurosci*, 6, 2155–2162.
Hendry IA & Campbell J (1976) *J. Neurocytol.*, 5, 351–360.
Hendry IA, Murphy M, Hilton D J, Nicola N A & Bartlett P F (1992) *J. Neurosci.* 12, 3427–3434.
Hunt et al., (1967) *Am. J. Surgery*, 114: 302–307.
Koch A E, Harlow L A, Haines G K, Amento E P, Unemoti E N, Wong W L, Pope R M, Ferrara N, (1994) *J. Immunol.* 152, 4149–4156.
Kromer A F (1987) *Science*, 235, 214–216.
Larsson C, Weber G, Kvanta E, Lewis C, Janson M, Jones C, Glaser T, Evans G, Nordenskjold M, (1992) *Hum. Genet.* 89, 187–193.
OZUS Leung D W, Cachianes G, Kuang W-J, Goeddel D V & Ferrara N (1989) *Science* 246:1306–1309.
Lowe C, Cornish J, Callon K, Martin T J & Reid I R (1991) *J. Bone Mineral Res.*, 6, 1277–1283.
Lowe C, Cornish J, Martin T J & Reid I R (1991) *Calcif. Tissue Int.*, 49, 394–397.
Martinou J C, Martinou I & Kato AC (1992) *Neuron*, 8, 737–744.
Maruta et al (1993) *Growth Factors* 8: 119–134.
Midy V & Plouet J (1994) *Biochem. Biophys. Res. Commun.*, 199: 380–386.
Miles A A & Miles EM (1952) *J. Physiol. (Lond)* 118:228–257.
Montesano R, Vassalli J D, Baird A, Guillemin R & Orci, L (1986) *Proc. Natl. Acad. Sci USA*, 83, 7297–7301.
Nurcombe et al (1992) *Development* 116: 1175–1183.
Otto D., Frotscher M & Unsicker K (1989) *J. Neurosci. Res.*, 22, 83–91.
Pepper M S, Ferrara N, Orci L, Montesano R. (1991) Biochem. Biophys. Res. Commun. 181, 902–906).
Rochell J M, Watson M L, Oakey R J and Seldin M F (1992) *Genomics* 14, 26–31.
Roth S & Weston J (1967) *Proc. Natl. Acad. Sci USA*, 58: 974–980.
Sambrook J, Fritsch E F, Maniatis, T, (1989) *Molecular Cloning: A Laboratory Manual— 2nd Ed.* Cold Spring Harbor Laboratory Press, Cold Spring Harbor, N.Y.
Santos M A (1991) *Nucleic Acids Res.* 19, 5442.
Schilling et al., (1959) *Surgery*, 46: 702–710.
Senger D R, Van De Water L, Brown L F, Nagy J A, Yeo K T, Yeo T K, Berse B, Jackman R W, Dvorak A M, Dvorak H F (1993) *Cancer Netastasis Rev.* 12, 303–324.
Sharkey A M, Charnock-Jones D S, Boocock C A, Brown K D, Smith S K, (1993) *J. Reprod Fertil.* 99. 609–615.
Sunderkotter C, Steinbrink K, Goebeler M, Bhardway R, Sorg E, (1993) *J. Leukocyt, Biol.* 55, 410–422.
Suter U, Angst C, Tien C-L, Drinkwater C C, Lindsay R M and Shooter E M (1992) *J. Neurosci.*, 12, 306–318.
Tischer E, Mitchell R, Hartman T, Silva M, Gospodarowicz D, Fiddes J C, & Abraham J (1991) J. Biol. Chem. 266, 11947–11954.
Williams L R, Varon S, Peterson G M, Wictorin K, Fischer W, Bjorklund A & Gage F H (1986) *Proc. Natl. Acad. Sci. USA* 83, 9231–9235.
Yan Z, Weich H A, Bemart W, Breckwoldt M, Neulen J, (1993) *J. Clin. Endocrinol. Metab.* 77, 1723–1725.
Yip N K, Rich K M, Lampe P A & Johnson E M Jr (1984) J. Neurosci., 4, 2986–2992.

What is claimed is:

1. An isolated polypeptide comprising an amino acid sequence of SEQ ID NO:8.
2. An isolated polypeptide comprising an amino acid sequence of SEQ ID NO:10.
3. A recombinant polypeptide comprising an amino acid sequence of SEQ ID NO:8.
4. A recombinant polypeptide comprising an amino acid sequence of SEQ ID NO:10.
5. An isolated polypeptide consisting of an amino acid sequence of SEQ ID NO:8.
6. An isolated polypeptide consisting of an amino acid sequence of SEQ ID NO:10.
7. A recombinant polypeptide consisting of an amino acid sequence of SEQ ID NO:8.
8. A recombinant polypeptide consisting of an amino acid sequence of SEQ ID NO:10.

* * * * *

UNITED STATES PATENT AND TRADEMARK OFFICE
CERTIFICATE OF CORRECTION

PATENT NO. : 7,160,991 B1 Page 1 of 1
APPLICATION NO. : 09/238088
DATED : January 9, 2007
INVENTOR(S) : Hayward et al.

It is certified that error appears in the above-identified patent and that said Letters Patent is hereby corrected as shown below:

Column 6, line 56, delete the text beginning with "FIG. 13" to and ending "0.015mm(D)." in Column 7, line 26.

Signed and Sealed this

Fifth Day of June, 2007

JON W. DUDAS
*Director of the United States Patent and Trademark Office*